US012733985B2

(12) United States Patent
Dos Santos Raposo et al.

(10) Patent No.: US 12,733,985 B2
(45) Date of Patent: Sep. 15, 2026

(54) AUTOMATIC PLACEMENT OF REFERENCE GRIDS AND ESTIMATION OF ANATOMICAL COORDINATE SYSTEMS

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Carolina Dos Santos Raposo, Coimbra (PT); João Pedro De Almeida Barreto, Coimbra (PT); Michel Gonçalves Almeida Antunes, Coimbra (PT)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 0 days.

(21) Appl. No.: 19/093,574

(22) Filed: Mar. 28, 2025

(65) Prior Publication Data

US 2025/0221775 A1 Jul. 10, 2025

Related U.S. Application Data

(62) Division of application No. 18/848,296, filed as application No. PCT/US2023/025970 on Jun. 22, 2023, now Pat. No. 12,285,221.

(Continued)

(51) Int. Cl.
*A61B 34/10* (2016.01)

(52) U.S. Cl.
CPC ........ *A61B 34/10* (2016.02); *A61B 2034/105* (2016.02)

(58) Field of Classification Search
CPC .......................... A61B 34/10; A61B 2034/105
See application file for complete search history.

(56) References Cited

U.S. PATENT DOCUMENTS 11,439,467 B1 * 9/2022 Park ...................... A61B 34/10
2009/0131941 A1 5/2009 Park et al.

(Continued)

FOREIGN PATENT DOCUMENTS

RU 2747534 C1 5/2021

OTHER PUBLICATIONS

Amis et al., Anterior cruciate ligament graft positioning, tensioning and twisting, Knee Surg Sports Traumatol Arthrosc., 1998; 6(Suppl 1):S2-S12, doi: 10.1007/s001670050215.

(Continued)

*Primary Examiner* — Rochelle D Turchen
(74) *Attorney, Agent, or Firm* — Dickinson Wright PLLC; Damian M. Aquino

(57) ABSTRACT

Disclosed are systems and methods for a computerized framework that provides novel mechanisms for determining the automatic placement of a reference grid and an anatomical reference frame (ARF) of a bone. The disclosed framework is operational for the enablement of computerized mechanisms that, based on a three-dimensional (3D) model of a distal femur, can determine, provide and/or display the anatomically correct positions of femoral tunnels and/or other forms of surgical landmarks surgeons rely on for anterior cruciate ligament (ACL) procedures. The disclosed framework is also operational for the enablement of computerized mechanisms that, based on a three-dimensional (3D) model of a proximal tibia, can determine, provide and/or display the anatomically correct positions of tibial tunnels and/or other forms of surgical landmarks surgeons rely on for ACL procedures.

20 Claims, 17 Drawing Sheets

Related U.S. Application Data

(60) Provisional application No. 63/354,953, filed on Jun. 23, 2022.

(56) References Cited

U.S. PATENT DOCUMENTS

| | | | | |
|---|---|---|---|---|
| 2009/0171355 | A1 | 7/2009 | Amis et al. | |
| 2010/0121175 | A1* | 5/2010 | Jolly ...................... | A61B 5/055 600/410 |
| 2013/0211531 | A1 | 8/2013 | Steines et al. | |
| 2016/0220312 | A1 | 8/2016 | Mahfouz | |
| 2016/0242935 | A1 | 8/2016 | Amis et al. | |
| 2017/0340389 | A1 | 11/2017 | Otto et al. | |
| 2019/0246944 | A1 | 8/2019 | Mahfouz | |
| 2020/0074748 | A1 | 3/2020 | de Almeida Barreto et al. | |
| 2021/0007806 | A1 | 1/2021 | Karade et al. | |
| 2021/0038234 | A1 | 2/2021 | Amis et al. | |
| 2022/0008219 | A1 | 1/2022 | Logan | |

OTHER PUBLICATIONS

Dabirrahmani et al., Comparison of isometric and anatomical graft placement in synthetic ACL reconstructions: A pilot study, Dec. 1, 2013 (Dec. 1, 2013), [retrieved on Oct. 6, 2023], Retrieved from the Internet: <URL: https://www.sciencedirect.com/science/article/pii/S0010482513002874, pp. 2287-2296.

Hodel et al., Influence of femoral tunnel exit on the 3D graft bending angle in anterior cruciate ligament reconstruction. Dec. 31, 2021 (Dec. 31, 2021), [retrieved on Oct. 7, 2023], Retrieved from the Internet: <URL: https://www.ncbi.nlm.nih.gov/pmc/articles/PMC8233443/pdf/40634_2021_Article_364.pdf, pp. 1-8.

International Search Report and Written Opinion mailed Nov. 2, 2023 for International Application No. PCT/US2023/025970, 18 pages.

* cited by examiner

AUTOMATIC PLACEMENT OF REFERENCE GRIDS AND ESTIMATION OF ANATOMICAL COORDINATE SYSTEMS

CROSS-REFERENCE TO RELATED APPLICATIONS

This application is a divisional of U.S. patent application Ser. No. 18/848,296, filed Sep. 18, 2024, which is a U.S. National Phase entry of PCT/US2023/25970, filed Jun. 22, 2023, titled "Automatic Placement of Reference Grids and Estimation of Anatomical Coordinate Systems." The PCT application claims the benefit of U.S. Provisional App. 63/354,953 filed Jun. 23, 2022 titled "Automatic Placement of Bernard-Hertel's Grid and Estimation of Anatomical Coordinate System in a 3D Model of a Distal Femur." Each of the applications above are incorporated by reference herein as if reproduced in full below.

TECHNICAL FIELD

The present disclosure relates to preoperative and intraoperative surgical analysis and processing, and more particularly, to methodologies for anatomical reference frame (ARF) determinations of a bone and the automatic placement of a reference grid, such as the Bernard-Hertel's (BH) grid and/or a tibial grid.

BACKGROUND

The Anterior Cruciate Ligament (ACL) is one of the key ligaments that provide stability to the knee joint. Playing sports that involve sudden stops or changes in direction is one of the main causes for ACL injury, an example of which is its complete tear. For this reason, an ACL tear is a common medical condition with more than 200,000 annual cases per year in the United States alone. The standard way of treatment is arthroscopic reconstruction where the torn ligament is replaced by a tissue graft that is pulled into the knee joint through tunnels opened with a drill in both the femur and tibia. Opening these tunnels in an anatomically correct position ensures knee stability and patient satisfaction, though the current failure rates in primary ACL reconstructions range from 10-15%.

The position and orientation of the femoral tunnel significantly impacts the success of the surgery, motivating the need for a pre-operative plan for properly defining the best femoral tunnel. Compared with the femoral side, significantly less attention is given to the surgical technique for accurate tibial tunnel creation. However, recent studies have emphasized the importance of the tibial tunnel position and revealed that tibial tunnel position influences the results of anatomical ACL reconstruction. Tibial tunnels placed too far anteriorly may lead to increased graft obliquity and subsequent impingement, whereas grafts placed too far posteriorly may lead to increased anterior translational laxity

SUMMARY

Referring initially the femur, in order to determine the anatomically correct position of the femoral tunnel in the related-art, some surgeons rely on specific anatomical landmarks. However, studies suggest that these landmarks are not reliable and may even not exist in some patients. In order to obtain more accurate femoral tunnel positions, a Bernard-Hertel's (BH) grid can be utilized. The BH grid can be utilized for proposing ACL reconstruction techniques and for assessing tunnel placement after ACL reconstruction.

By way of background, BH grids involve a quadrant method for determining the location of the femoral insertion. Using a lateral radiograph, the Blumensaat's line can be identified and two other lines perpendicular to that one can be drawn such that the lines go through the shallow and the deep borders of the lateral femoral condyle. A fourth line to be drawn is parallel to Blumensaat's line and is tangent to the inferior border of the condyles. The obtained BH grid consists of a normalized reference frame that is independent of knee size, shape and distance at which the X-ray was acquired. Coordinates on this reference frame are given as percentages along Blumensaat's line and the perpendicular direction.

Some current studies suggest that, besides tunnel position, the orientation of the femoral tunnel can also play an important role in the success of the ACL reconstruction surgery. Tunnel orientation is defined as a direction with respect to the three anatomical directions (i.e., sagittal, axial and coronal), which define the anatomical reference frame (ARF) and/or anatomical coordinate system (ACS).

Accordingly, the disclosed systems and methods provide a novel framework that, given a three-dimensional (3D) model of a distal femur, automatically places a BH grid and determines the ARF of the bone. The disclosed methodology is applicable to different femur shapes and sizes, and reliable to replace the manual process with negligible error.

Indeed, the BH grid system was originally applied to lateral radiographs of the knee, and recent works still make use of this approach. However, there are studies that show that the image quality and the direction of the X-ray tube with respect to the patient can influence the accuracy of tunnel location measurement. Also, there have been observed instances that computerized tomography (CT) imaging may be more reliable for performing this task. The common aspect between all the related-art methodologies is that the placement of BH grid, whether using radiographs or CT imaging, is a manual process that suffers from observer variability. For example, despite an apparent improved inter-observer agreement obtained with CT scans (when compared to radiographs), the variability in measuring the femoral tunnel location is still non-negligible, making such process unreliable.

There currently exist several related-art methods for estimating the ARF from a 3D model of a femur in an automatic manner, which are assumed to be more reliable than manual approaches especially due to the elimination of intra- and inter-observer variability. These automatic related-art methods rely on a template model or atlas, make use of the entire femur, including the femoral head, and/or perform cylinder/sphere or ellipse fitting to the posterior condyles. Despite being fully automatic and presenting good reliability, by being dependent on a prior knowledge (e.g., a pre-constructed model of the entire femur and/or template model/atlas), the related-art approaches require more information than the disclosed methodology, and are less general and more prone to suffer from local minima issues. In addition, by retrieving the sagittal direction through cylinder/sphere/ellipse fitting to the condyles, it is not guaranteed that the direction yields a lateral radiographic view in which both condyles perfectly overlap, which is used for applying the BH grid system.

For this reason, among others, related-art automatic ARF estimation methods are not suitable for replacing the sagittal direction estimation step in automatic BH grid placement algorithms. For example, a related-art approach attempted to provide the automatic estimation of the ARF without the need of knowledge of the entire femur model. However, not only is this approach not suitable for generating the sagittal direction, the approach also does not guarantee overlap of the condyles. Moreover, the approach is not reliably capable of determining the axial direction.

The present disclosure remedies these shortcomings, at least in part, by providing a computerized methodology that, given a 3D model of a distal femur, automatically provides the placement of BH grid and determines the ARF. According to some embodiments, as discussed in more detail below, the disclosed methodology operates by determining the sagittal direction through alignment of the medial and lateral condyles, and then generates a radiographic view of the distal femur for detecting the intercondylar contour. A BH grid is then obtained as the rectangle that is tangent to this contour and encloses the radiographic view of one or both condyles.

Thus, improved mechanisms are disclosed, which provide novel ways to improve the efficiency and accuracy for placement and reliance of a BH grid. For example, tunnel entry points obtained with via the disclosed automatic processing methodology (e.g., algorithm) on 21 different femur models differ from the manual process by an average of 0.28 mm+−0.16 mm. This error is about seven (7) times smaller than the smallest errors reported for existing automatic and manual methods.

According to some embodiments, the disclosed methodology continues by determining the axial direction automatically by using the estimated sagittal plane for retrieving a sagittal view of the bone shaft, from which circles can be extracted. By joining the center of these circles, the axial direction is obtained. The cross-product between the sagittal and axial directions yields the coronal one, providing the complete ARF.

Unlike the related-art methods for automatic estimation of BH grid, the disclosed and deployed methodology does not require alignment with a template model, thereby evidencing operations that work with less information and assumptions, which enables the finding of the sagittal direction in a more efficient and accurate manner, without the need for initialization. Indeed, as discussed herein, the disclosed methodology is not prone to suffer from local minima issues. Also, the disclosed detection of Blumensaat's line does not depend on the curvature pattern of the intercondylar contour, thereby enabling it to be applicable to different types of morphologies. Similarly, comparing to the existing automatic approaches for ARF estimation, the disclosed, executable methodology does not require prior information, nor does it require entire femur models, which enables it to be applicable to a wider variety of input models.

Turning now to the tibia, measuring the position of the tibial tunnel has been recently accomplished using a 3D model of a proximal tibia, obtained from a CT scan or a three-dimensional volume-rendering image, in which a rectangular grid is placed such that it encloses the tibial plateau, when considering an axial view of the bone. This approach is referred to as the quadrant method. The first step of the algorithm is to define the axial direction, which is considered as the normal to the tibial plateau. Then, from an axial view of the tibia, the approach finds the line that is bi-tangent to the posterior contour of the plateau and the remainder of the grid is obtained such that the rectangle's sides are tangent to the anterior, medial, and lateral contours of the plateau. The obtained grid consists of a normalized reference frame that is independent of knee size and shape. Coordinates in this reference frame are given as percentages along the anterior-posterior (AP) and the medial-lateral (ML) directions.

The purpose of the tibial grid is to locate the interior point of the ACL tibial tunnel. In order to fully define the tunnel, the exterior point is also determined. Recent works consider the location of the tibial tuberosity for the task of finding the exterior point, claiming that the exterior point should be 1 cm to 2 cm medial to the tibial tubercle.

Related-art approaches for defining and measuring the location of the tibial tunnel also rely on radiographs of the knee. However, recent studies also show that use of radiographs may be unreliable due to inadequate position of the knee with respect to the X-ray tube, and that CT scans and three-dimensional volume rendering images provide results that are more reliable. Having a 3D model of a proximal tibia, the quadrant method has been the most widely used related-art technique for measuring the position of the interior point of the tibial tunnel. A common aspect between many related-art techniques is that the placement of the tibial grid is a manual process, being time-consuming and inevitably suffering from observer variability.

The location of the tibial tuberosity may be used to decide about the exterior aperture of the tibial tunnel, and in many cases is determined by visual observation of the patient.

This document discloses a method that, given a 3D model of a proximal tibia, automatically provides the placement of the tibial grid, the anatomical reference frame of the tibia, and the location of tibial tuberosity. The method is robust to different tibia shapes and sizes and reliable enough to replace the manual process with negligible error.

The disclosed systems and methods provide a computerized framework that addresses current shortcomings in the existing technologies, inter alia, by providing novel mechanisms for automatic placement of the BH grid, the tibial grid, and automatic determination of an ARF for femur and tibia.

In accordance with one or more embodiments, the present disclosure provides a non-transitory computer-readable storage medium for carrying out the above-mentioned technical steps. The non-transitory computer-readable storage medium has tangibly stored thereon, or tangibly encoded thereon, computer readable instructions that, when executed by a device, cause at least one processor to perform a method for providing novel mechanisms for automatic placement of the BH grid and automatic determination of an ARF.

In accordance with one or more embodiments, a system is provided that comprises one or more computing devices and/or apparatus configured to provide functionality in accordance with such embodiments. In accordance with one or more embodiments, functionality is embodied in steps of a method performed by at least one computing device and/or apparatus. In accordance with one or more embodiments, program code (or program logic) executed by a processor(s) of a computing device to implement functionality in accordance with one or more such embodiments is embodied in, by and/or on a non-transitory computer-readable medium.

BRIEF DESCRIPTION OF THE DRAWINGS

The features and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure:

FIG. 15 shows a perspective view of a rendering of the 3D model including a tibial plane.

FIG. 16 shows a side elevation view of a rendering of the 3D model including the tibial plane.

DETAILED DESCRIPTION

Figure 1:
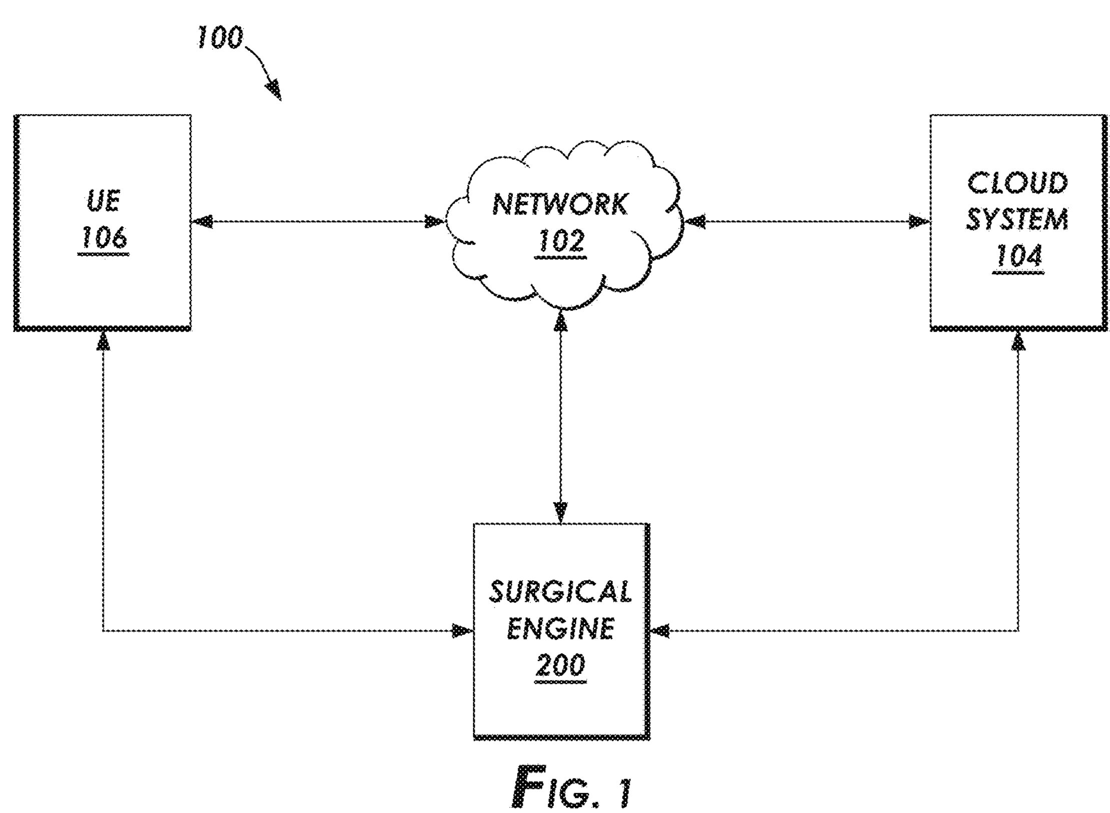
FIG. 1 is a block diagram of an example configuration within which the systems and methods disclosed herein could be implemented according to some embodiments of the present disclosure.

The present disclosure will now be described more fully hereinafter with reference to the accompanying drawings, which form a part hereof, and which show, by way of non-limiting illustration, certain example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure is described below with reference to block diagrams and operational illustrations of methods and devices. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer to alter its function as detailed herein, a special purpose computer, ASIC, or other programmable data processing apparatus, such that the instructions, which execute via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as "up," "down," "bottom,"

"top," "front," "rear," "upper," "lower," "upwardly," "downwardly," and other orientational descriptors are intended to facilitate the description of the exemplary embodiments of the present disclosure, and are not intended to limit the structure of the exemplary embodiments of the present disclosure to any particular position or orientation. Terms of degree, such as "substantially" or "approximately," are understood by those skilled in the art to refer to reasonable ranges around and including the given value and ranges outside the given value, for example, general tolerances associated with manufacturing, assembly, and use of the embodiments. The term "substantially," when referring to a structure or characteristic, includes the characteristic that is mostly or entirely present in the characteristic or structure.

For the purposes of this disclosure, a non-transitory computer readable medium (or computer-readable storage medium/media) stores computer data, which data can include computer program code (or computer-executable instructions) that is executable by a computer, in machine-readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, optical storage, cloud storage, magnetic storage devices, or any other physical or material medium which can be used to tangibly store the desired information or data or instructions and which can be accessed by a computer or processor.

For the purposes of this disclosure, the term "server" should be understood to refer to a service point that provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

For the purposes of this disclosure, a "network" should be understood to refer to a network that may couple devices so that communications may be exchanged, such as between a server and a client device or other types of devices, including between wireless devices coupled via a wireless network, for example. A network may also include mass storage, such as network attached storage (NAS), a storage area network (SAN), a content delivery network (CDN) or other forms of computer or machine-readable media, for example. A network may include the Internet, one or more local area networks (LANs), one or more wide area networks (WANs), wire-line type connections, wireless type connections, cellular or any combination thereof. Likewise, sub-networks, which may employ differing architectures or may be compliant or compatible with differing protocols, may interoperate within a larger network.

For purposes of this disclosure, a "wireless network" should be understood to couple client devices with a network. A wireless network may employ stand-alone ad-hoc networks, mesh networks, Wireless LAN (WLAN) networks, cellular networks, or the like. A wireless network may further employ a plurality of network access technologies, including Wi-Fi, Long Term Evolution (LTE), WLAN, Wireless Router (WR) mesh, or 2nd, 3rd, $4^{th}$ or $5^{th}$ generation (2G, 3G, 4G or 5G) cellular technology, mobile edge computing (MEC), Bluetooth, 802.11b/g/n, or the like. Network access technologies may enable wide area coverage for devices, such as client devices with varying degrees of mobility, for example. In short, a wireless network may include virtually any type of wireless communication mechanism by which signals may be communicated between devices, such as a client device or a computing device, between or within a network, or the like.

A computing device may be capable of sending or receiving signals, such as via a wired or wireless network, or may be capable of processing or storing signals, such as in memory as physical memory states, and may, therefore, operate as a server. Thus, devices capable of operating as a server may include, as examples, dedicated rack-mounted servers, desktop computers, laptop computers, set top boxes, integrated devices combining various features, such as two or more features of the foregoing devices, or the like.

For purposes of this disclosure, a client (or consumer or user) device, referred to as user equipment (UE)), may include a computing device capable of sending or receiving signals, such as via a wired or a wireless network. A client device may, for example, include a desktop computer or a portable device, such as a cellular telephone, a smart phone, a display pager, a radio frequency (RF) device, an infrared (IR) device a Near Field Communication (NFC) device, a Personal Digital Assistant (PDA), a handheld computer, a tablet computer, a phablet, a laptop computer, a set top box, a wearable computer, smart watch, an integrated or distributed device combining various features, such as features of the forgoing devices, or the like.

In some embodiments, as discussed below, the client device can also be, or can communicatively be coupled to, any type of known or to be known medical device (e.g., any type of Class I, II or III medical device), such as, but not limited to, a MRI machine, CT scanner, Electrocardiogram (ECG or EKG) device, photopletismograph (PPG), Doppler and transmit-time flow meter, laser Doppler, an endoscopic device neuromodulation device, a neurostimulation device, and the like, or some combination thereof.

System or Framework

With reference to FIG. 1, system (or framework) 100 is depicted which includes a UE 106 (e.g., a client device), a network 102, a cloud system 104, and a surgical engine 200. The UE 106 can be any type of device, such as, but not limited to, a mobile phone, tablet, laptop, personal computer, sensor, Internet of Things (IoT) device, autonomous machine, and any other device equipped with a cellular, wireless, or wired transceiver. In some embodiments, as discussed above, the UE 106 can also be a medical device, or another device that is communicatively coupled to a medical device, that enables reception of readings from sensors of the medical device. For example, in some embodiments, the UE 106 can be a user's smartphone (or office/hospital equipment, for example) that is connected via WiFi, Bluetooth Low Energy (BLE) or NFC, for example, to a peripheral neuromodulation device. Thus, in some embodiments, the UE 106 can be configured to receive data from sensors associated with a medical device, as discussed in more detail below. Further discussion of the UE 106 is provided below at least in reference to FIGS. 10A and 10B.

Network 102 can be any type of network, such as, but not limited to, a wireless network, cellular network, the Internet, a local-area network, or a wide-area network. As discussed herein, network 102 can facilitate connectivity of the components of system 100, as illustrated in FIG. 1.

The cloud system 104 can be any type of cloud operating platform and/or network based system upon which applications, operations, and/or other forms of network resources can be located. For example, system 104 can correspond to a service provider, network provider and/or medical provider from where services and/or applications can be accessed, sourced or executed from. In some embodiments, the cloud system 104 can include a server(s) and/or a database of information that is accessible over network 102. In some embodiments, a database (not shown) of system 104 can store a dataset of data and metadata associated with local and/or network information related to a user(s) of the UE 106, patients and the UE 106, and the services and applications provided by cloud system 104 and/or surgical engine 200.

The surgical engine 200, as discussed below in more detail, includes components for determining the automatic placement of a reference grid for a bone, such as BH grid and an ARF associated tunnel placement through the femur, or a reference grid and ARF associated tunnel placement through the tibia. Embodiments of how engine 200 operates and functions, and the capabilities it includes and executes, among other functions, are discussed in more detail below in relation to FIGS. 3-8.

According to some embodiments, surgical engine 200 can be a special purpose machine or processor and could be hosted by a device on network 102, within cloud system 104 and/or on UE 106. In some embodiments, engine 200 can be hosted by a peripheral device connected to the UE 106 (e.g., a medical device, as discussed above).

According to some embodiments, surgical engine 200 can function as an application provided by cloud system 104. In some embodiments, engine 200 can function as an application installed on the UE 106. In some embodiments, such application can be a web-based application accessed by the UE 106 over network 102 from cloud system 104 (e.g., as indicated by the connection between network 102 and engine 200, and/or the dashed line between the UE 106 and engine 200 in FIG. 1). In some embodiments, engine 200 can be configured and/or installed as an augmenting script, program or application (e.g., a plug-in or extension) to another application or program provided by cloud system 104 and/or executing on the UE 106.

Figure 2:
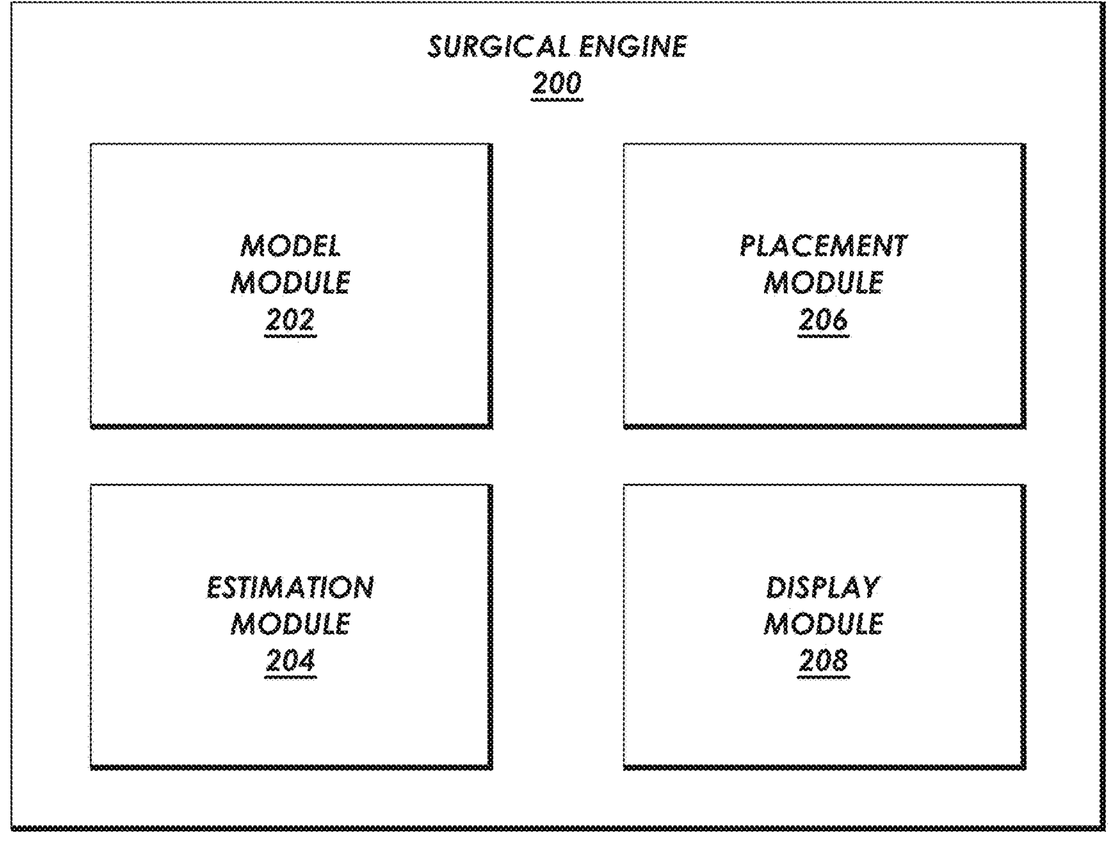
FIG. 2 is a block diagram illustrating components of an exemplary system according to some embodiments of the present disclosure.

As illustrated in FIG. 2, according to some embodiments, surgical engine 200 includes a model module 202, an estimation module 204, a placement module 206, and a display module 208. It should be understood that the engine (s) and modules discussed herein are non-exhaustive, as additional or fewer engines and/or modules (or sub-modules) may be applicable to the embodiments of the systems and methods discussed. More detail of the operations, configurations and functionalities of engine 200 and each of its modules, and their role within embodiments of the present disclosure will be discussed below. The specification first turns to processes associated with the femur.

Reference Grid and Anatomical Reference for the Femur

Figure 3:
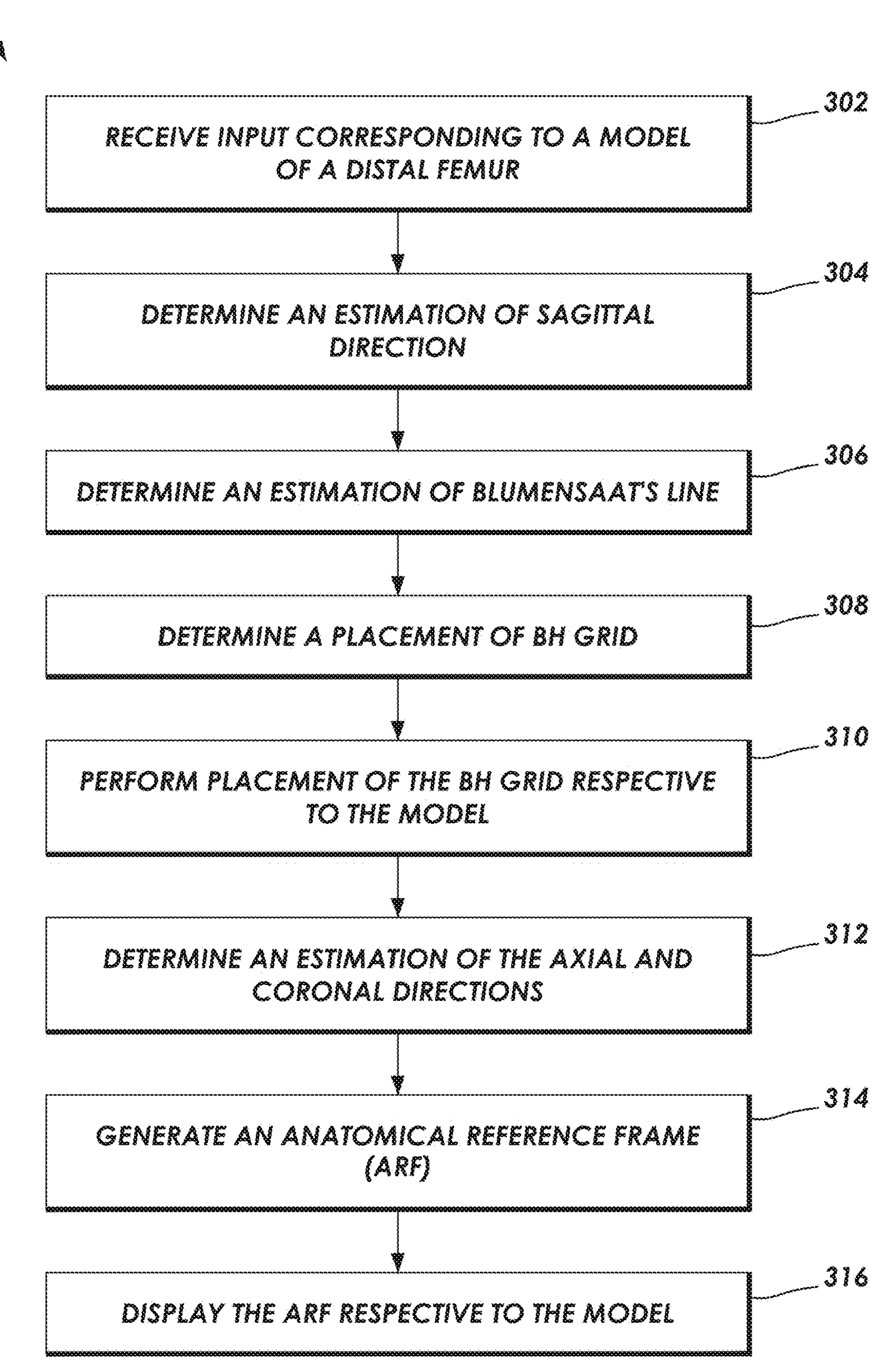
FIG. 3 illustrates an exemplary data flow according to some embodiments of the present disclosure.

Turning to FIG. 3, depicted is a Process 300 which details non-limiting example embodiments of the disclosed framework's computerized operations for determining an ARF of a bone pursuant to the automatic placement of a BH grid.

According to some embodiments, as discussed herein, framework (e.g., engine 200) can execute a methodology (as provided via at least Process 300) that operates by determining the sagittal direction through alignment of the medial and lateral condyles, and then generates a radiographic view of the distal femur for detecting the intercondylar contour. A BH grid is then obtained as the rectangle that is tangent to this contour and encloses the radiographic view of one or both condyles. The disclosed methodology continues by determining the axial direction automatically by using the estimated sagittal plane for retrieving a sagittal view of the bone shaft, from which circles can be extracted. By robustly joining the center of these circles, the axial direction is obtained. The cross-product between the sagittal and axial directions yields the coronal one, providing the complete ARF.

The disclosed framework, realized via engine 200's execution of the operations detailed as part of Process 300, is applicable to different femur shapes and sizes, and its improved reliability, accuracy and ease of implementation can replace the conventional processing medical upon which professionals currently rely.

According to some embodiments, Step 302 of Process 300 can be performed by model module 202 of surgical engine 200; Steps 304-306 and 310-312 can be performed by estimation module 204; Steps 308 and 314 can be performed by placement module 206; and Step 316 can be performed by display module 208.

Process 300 begins with Step 302 where engine 200 receives input that identifies a 3D model of a distal femur. According to some embodiments, the identification of the 3D model can be based on, but not limited to, a request to generate a 3D model, the search for and retrieval of a 3D model, and/or an upload and/or download of a 3D model. In some embodiments, the input can be in the form an image, message, multi-media item, and/or any other type of known or to be known format for engine 200 to receive and process for display a digital content corresponding to a model (e.g., 3D model) of a patient's bone, and particularly the distal femur.

It should be understood that while the discussion herein will focus on a 3D model of a distal femur, it should be construed as limiting, as other types, formats, and forms of models of other types of bones (e.g., proximal tibia, discussed below) can be utilized without departing from the scope of the instant disclosure.

In Step 304, engine 200 performs an estimation of the sagittal direction based on the received input from Step 302. According to some embodiments, Step 304 involves engine 200 estimating (e.g., not registering or initializing, as in conventional methodologies) the sagittal direction of the bone based on pairs of points whose normal vectors are orthogonal to the vector joining them. According to some embodiments, this is illustrated in example 400 in FIG. 4 where the example distal femur 402 has identified thereon pairs of points $P_1$ and $P_2$ and normal vectors $N_1$ and $N_2$, respectively.

According to some embodiments, Step 304 can involve, based on the input of the 3D model, computing a normal for every point (or at least a set of points on the bone). According to some embodiments, Step 304 can be restricted in the search domain when searching for points by finding a region of interest (ROI) that contains the condyle surface, where only points on that ROI (instead of the full 3D model) are considered. In some embodiments, ROI can be found by registering the 3D model with a template model, by making use of a statistical shape model (SSM), through 3D curvature analysis, using deep learning frameworks, or some combination thereof.

Figure 4:
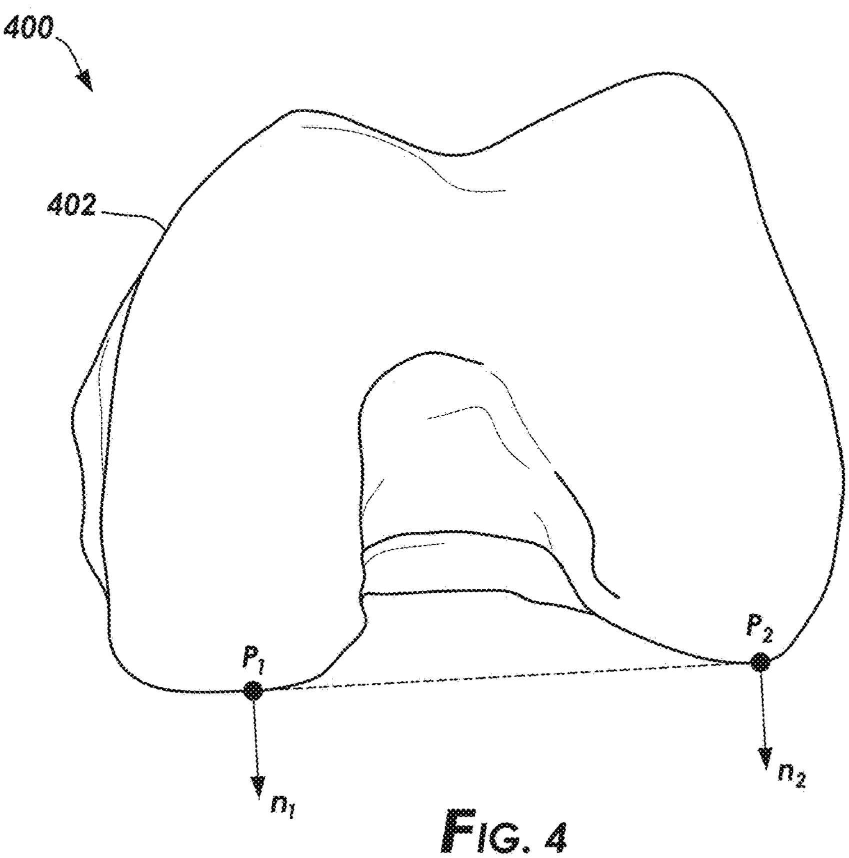
FIG. 4 depicts a non-limiting example embodiment of the disclosed technology according to some embodiments of the present disclosure.

Engine 200 can then analyze the computed normals and determine a pair of points (e.g., $P_1$ and $P_2$) for which the corresponding normals ($N_1$ and $N_2$) are parallel, and vector "v" joining $P_1$ and $P_2$ is orthogonal to $N_1$ and $N_2$, as illustrated in FIG. 4.

Engine 200 can then determine the sagittal direction based on the hypothesis: $v=P_2-P_1$. According to some embodiments, the vector v joining each selected pair of points consists of a hypothesis for the sagittal direction. Based on such sagittal direction hypotheses, an estimation of the sagittal direction can be determined. In some embodiments, the hypotheses can be represented as 3D points and then clustered, whereby a median value of the cluster can be computed. In some other embodiments, Random Sample Consensus (RANSAC), or other robust estimation models (e.g., Hough transform) can be applied to the set of hypotheses to estimate the sagittal direction.

According to some embodiments, Step 304 can further involve determining a lateral-to-medial orientation to the sagittal direction by identifying lateral and medial condyles (e.g., respective to $P_1$ and $P_2$).

In some embodiments, the estimation of the sagittal direction of Step 304 can further involve refining the sagittal direction by generating a simulated radiographic view of the femur or a two-dimensional (2D) intersection map (as discussed below in relation to at least Step 306 and FIG. 5), and adjusting the outer border of the condyles such that they overlap. Such generated views/maps can be generated by considering orthographic or perspective projections.

Figure 5:
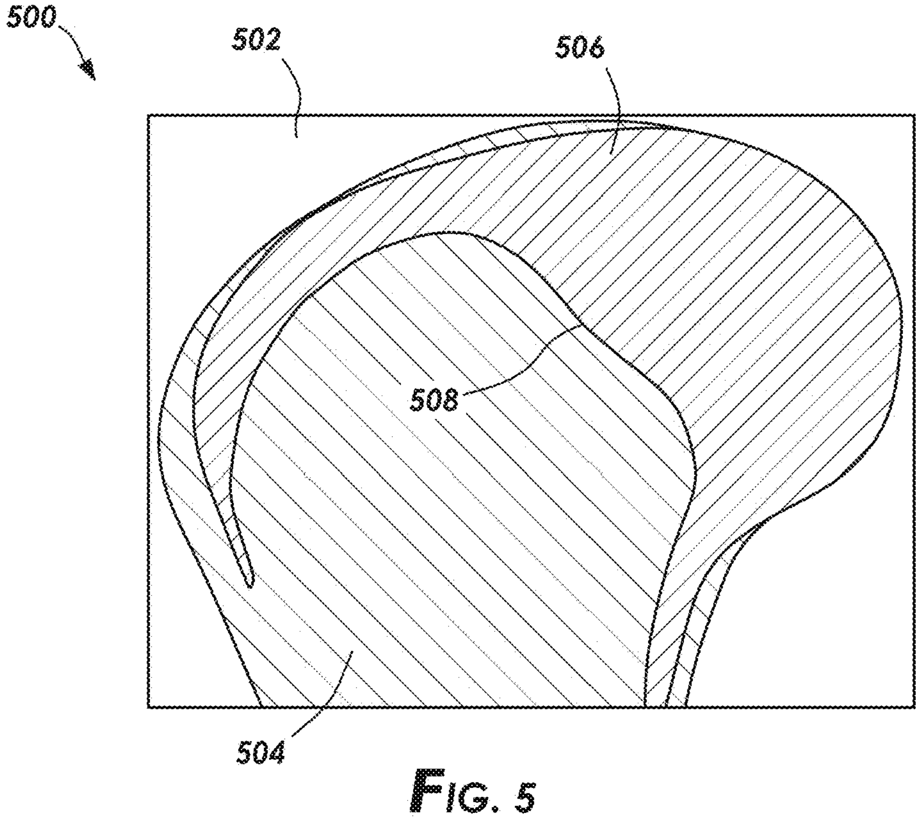
FIG. 5 depicts a non-limiting example embodiment of the disclosed technology according to some embodiments of the present disclosure.

Process 300 proceeds from Step 304 to Step 306 where, having determined the estimation of the sagittal direction (Step 304), engine 200 performs an estimation of Blumensaat's line. According to some embodiments, engine 200 accesses the 3D model of the femur, and builds a 2D projection of the number of intersections of projection rays with the 3D model (referred to as the "intersection map"). A non-limiting example of such mapping is provided in FIG. 5, where intersection map 500 includes regions 502, 504, and 506, and a curve 508. As depicted in FIG. 5, region 502 corresponds to zero (0) intersections, region 504 corresponds to regions with two (2) intersections, and region 506 corresponds to regions with four (4) intersections. According to some embodiments, intersection map 500 enables the identification of a curve 508 (e.g., curve "C"). Curve 508 corresponds to the contour of the intercondylar region, which can be determined by performing an edge detection analysis (or computation) and retrieving the curve between regions with intersections 2 and 4 (e.g., between regions 504 and 506, respectively, in FIG. 5).

According to some embodiments, the determination at Step 306 of Blumensaat's line can involve finding the line that is tangent to the curve 508 in the largest number of points that does not intersect it. In other words, regardless of shape, Blumensaat's line is tangent to curve 508 but does not intersect curve 508 despite being tangential. This is a novel executable step compared to different types of existing Blumensaat's line morphologies in that, unlike previous methods, it is not dependent on particular curvature patterns.

Figure 6:
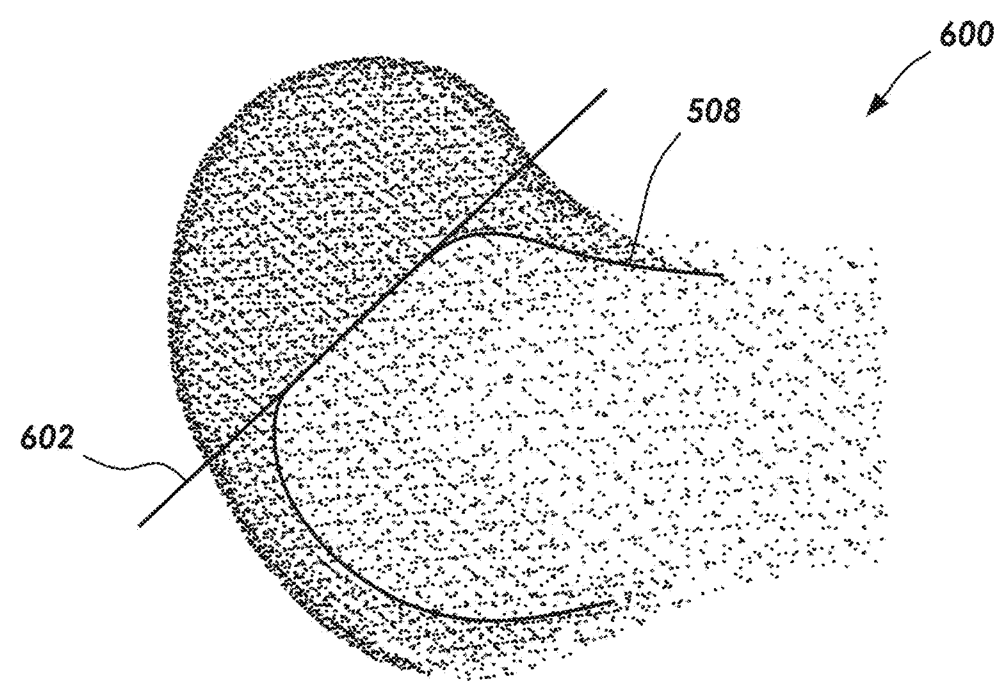
FIG. 6 depicts a non-limiting example embodiment of the disclosed technology according to some embodiments of the present disclosure.

Turning to FIG. 6, illustrated in 2D projection 600 of a distal femur from a side view, where Blumensaat's line 602 is shown in relation to curve 508. Thus, as depicted in FIG. 6 and described herein in relation to Step 306, Blumensaat's line is tangent to curve 508 in the largest number of points and does not intersect curve 508 elsewhere. According to some embodiments, Blumensaat's line can be determined based on the use of a template model/SSM, 2D curvature analysis, deep learning scheme, voting scheme, clustering, and/or any other type of known or to be known heuristics.

In some embodiments, in situations where curve 408 is a hill type, Blumensaat's line can intersect some region of the intercondylar contour and be tangent to it only in a specified location (e.g. near the intercondylar notch). In some embodiments, Blumensaat's line can be further based on a backprojection of the 2D points of intersection map 500 to points on the 3D model. In some embodiments, the backprojection can be based on a sectioning plane defined by the sagittal direction (from Step 304). Thus, according to some embodiments, 3D points in the 3D model can be retrieved/determined by backprojecting the intercondylar contour/Blumensaat's line onto the 3D model. Having such points, an appropriate sectioning plane of the model can be obtained based on, for example, the plane with sagittal direction that contains such points. In some embodiments, such sectioning plane can then be used when determining the axial direction through circle fitting in the shaft, as discussed below.

Process 300 then proceeds from Step 306 to Step 308 where engine 200 determines a placement of a BH grid. Engine 200 determines the placement (and other characteristics, such as, for example, size, proportions and dimensions) of the BH grid on the estimates for the sagittal direction (from Step 304) and Blumensaat's line (from Step 306).

Figure 7:
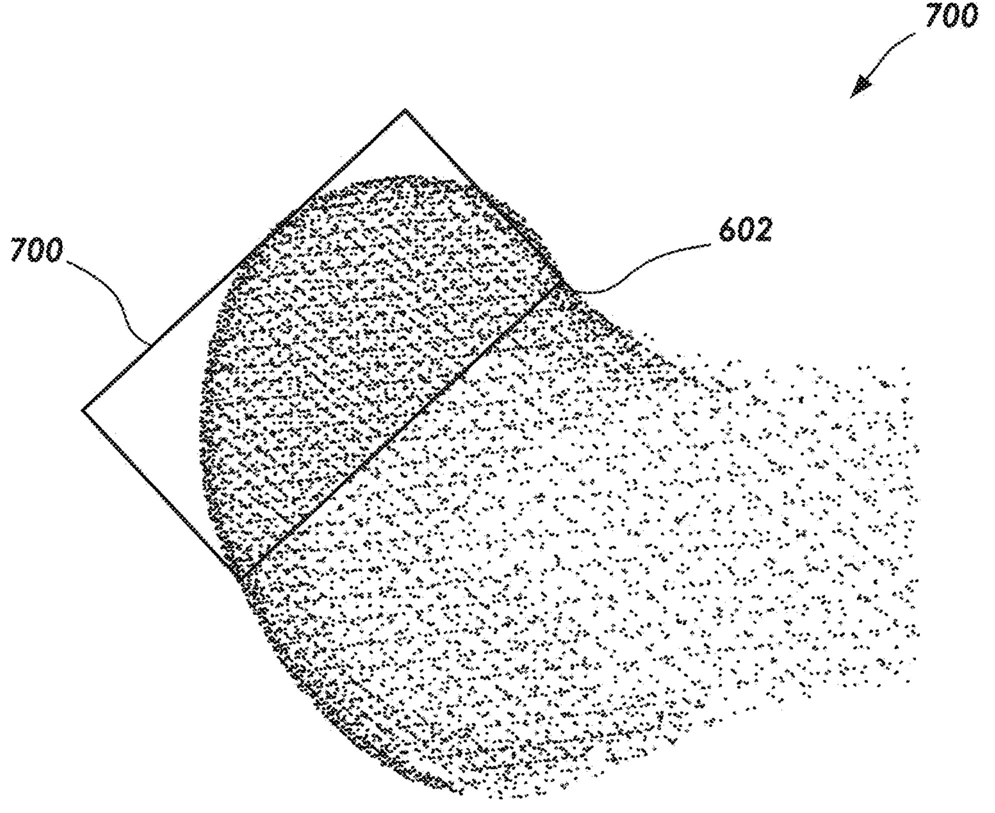
FIG. 7 depicts a non-limiting example embodiment of the disclosed technology according to some embodiments of the present disclosure.

According to some embodiments, Step 308 involves engine 200 placing the BH grid such that it encloses the condyles when depicted in a lateral view of the distal femur. According to some embodiments, edge detection is applied to an intersection map (e.g., map 500 from FIG. 5), where the edge corresponding to the curve enclosing the region of zero intersections is retrieved (which corresponds to the sagittal contour of the condyles). In other words, engine 200 utilizes a 2D projection of the number of intersections of projection rays along the sagittal direction with the bone model when considering an orthographic projection. Then, Blumensaat's line (line 602 from FIG. 6) is intersected with the obtained contour, yielding the long edge of BH grid. Finally, the line parallel to Blumensaat's line that is tangent to the contour is obtained, and the distance between both lines is the length of the short edge (width) of BH grid. An example of this is depicted in FIG. 7, wherein a 2D projection 700 is depicted, which includes Blumensaat's line 602 and BH grid 702. According to some embodiments, projection 700 can be a radiographic view or an intersection map obtained from either an orthographic or perspective projection. In some embodiments, if the location of the lateral condyle is known, edge detection of Step 306 can be accomplished by firstly sectioning the model sagittally and considering only the lateral condyle for building the intersection map.

In some embodiments, Step 308 can further involve backprojecting the BH grid from the 2D model to the 3D model. In such embodiments, which is realized in Step 310, engine 200 can perform the backprojection so that the BH grid is displayed as part of or as an overlay of the 3D model. In some embodiments, the backprojection can be based on a sectioning plane defined by the sagittal direction and Blumensaat's line.

Process 300 then proceeds from Step 310 to Step 312 where engine 200 an estimation of the axial and coronal directions (e.g., remaining anatomical directions) are determined. As discussed herein, the axial and coronal directions are utilized to determine ARF.

According to some embodiments, Step 312 can include a set of sub-steps. A first sub-step involves engine 200 obtaining a sagittal view of the bone from which the contours of the shaft are retrieved. In some embodiments, the sagittal view can be an orthographic projection of the entire or sectioned femur model, or obtained from intersection of the sectioning plane with the model. In some embodiments, the sagittal view can be an intersection map (as described above in relation to FIG. 5), where the contour of the shaft can be obtained based on the transition between regions of 0 and 2 intersections (e.g., region 502 and 504, respectively).

In the next sub-step, engine 200 performs a search for the circles that are tangent (e.g., simultaneously tangent) to the shaft contour in two points, where the line that joins the centers of the obtained circles provides an estimate for the axial direction. In some embodiments, in cases where the anterior and posterior cortices of the femur are known, the search can be restricted by considering only pairs containing one point from each cortex. According to some embodiments, the axial direction can be alternatively determined based on a determined relationship between a fixed angle (at a predetermined value) with respect to Blumensaat's line. In some embodiments, the axial direction can be alternatively determined based on a cylinder fitting methodology utilizing dimensions and values of the shaft region.

Engine 200 can then determine the coronal direction via the cross-product between the sagittal and axial directions.

Figure 8:
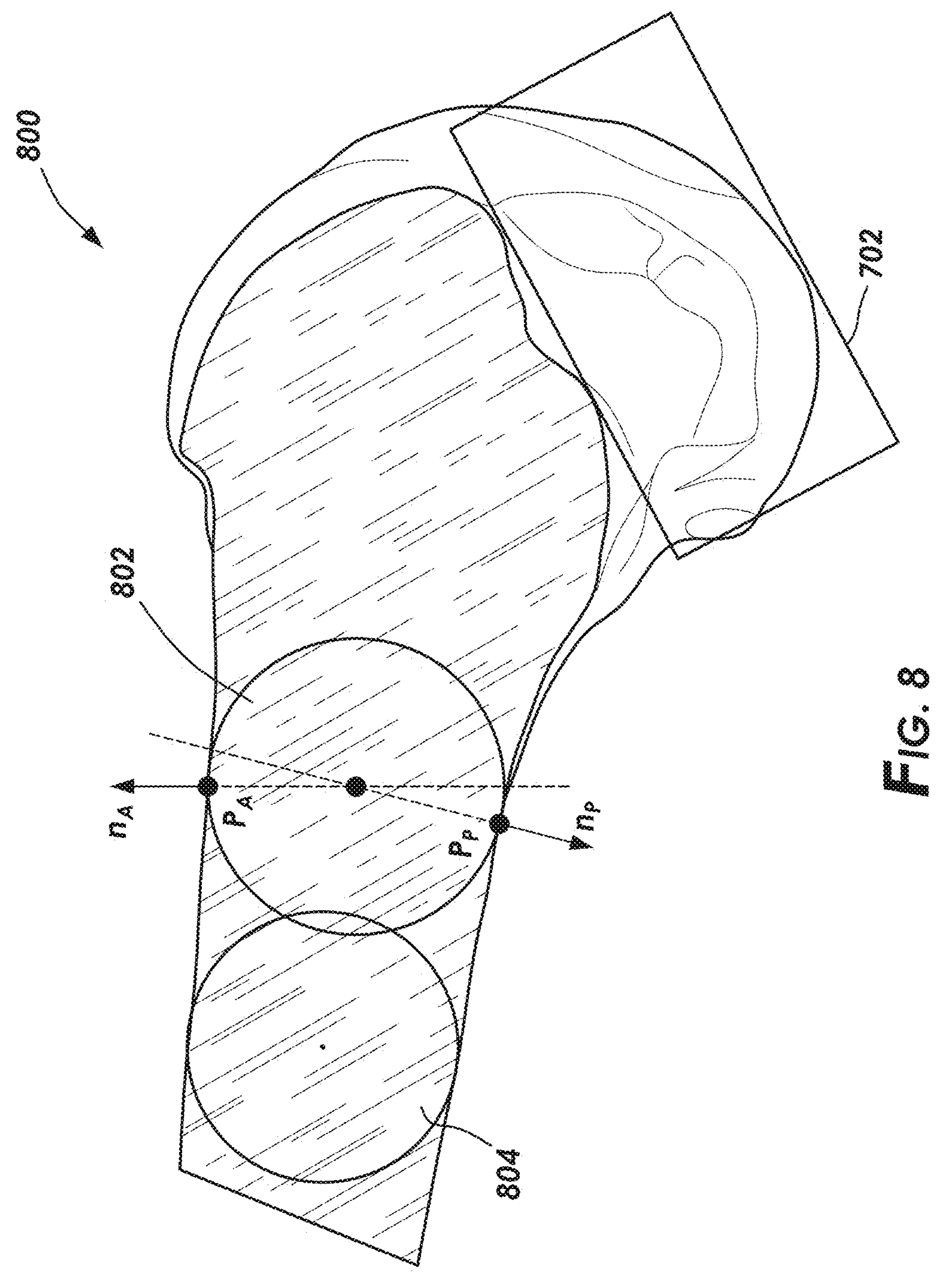
FIG. 8 depicts a non-limiting example embodiment of the disclosed technology according to some embodiments of the present disclosure.

FIG. 8 depicts an example of a femur model 800, where circles 802 and 804 are depicted. Circles 802 and 804, as discussed above, are tangent to the shaft contour and can be obtained as follows. First, the normal at each point in the shaft contour is computed. Then, all pairs of contour points are generated and the lines going through them that are parallel to the respective normal vectors are intersected. According to FIG. 8, the line with direction na that contains point PA intersects with the line with direction np that contains point Pp on the center of circle 802, which belongs to the axial direction. By joining all intersection points that are equidistant from the considered points, which correspond to centers of circles tangent to the shaft contour, the axial direction is obtained.

According to some embodiments, the step of joining the points can be performed using any known or to be known technique, algorithm or mechanism, such as, but not limited to, standard or robust line fitting, clustering schemes, Hough transforms, and/or any other known or to be known technique for estimating and determining lines (and their distances/length) from sets of points.

Figure 9:
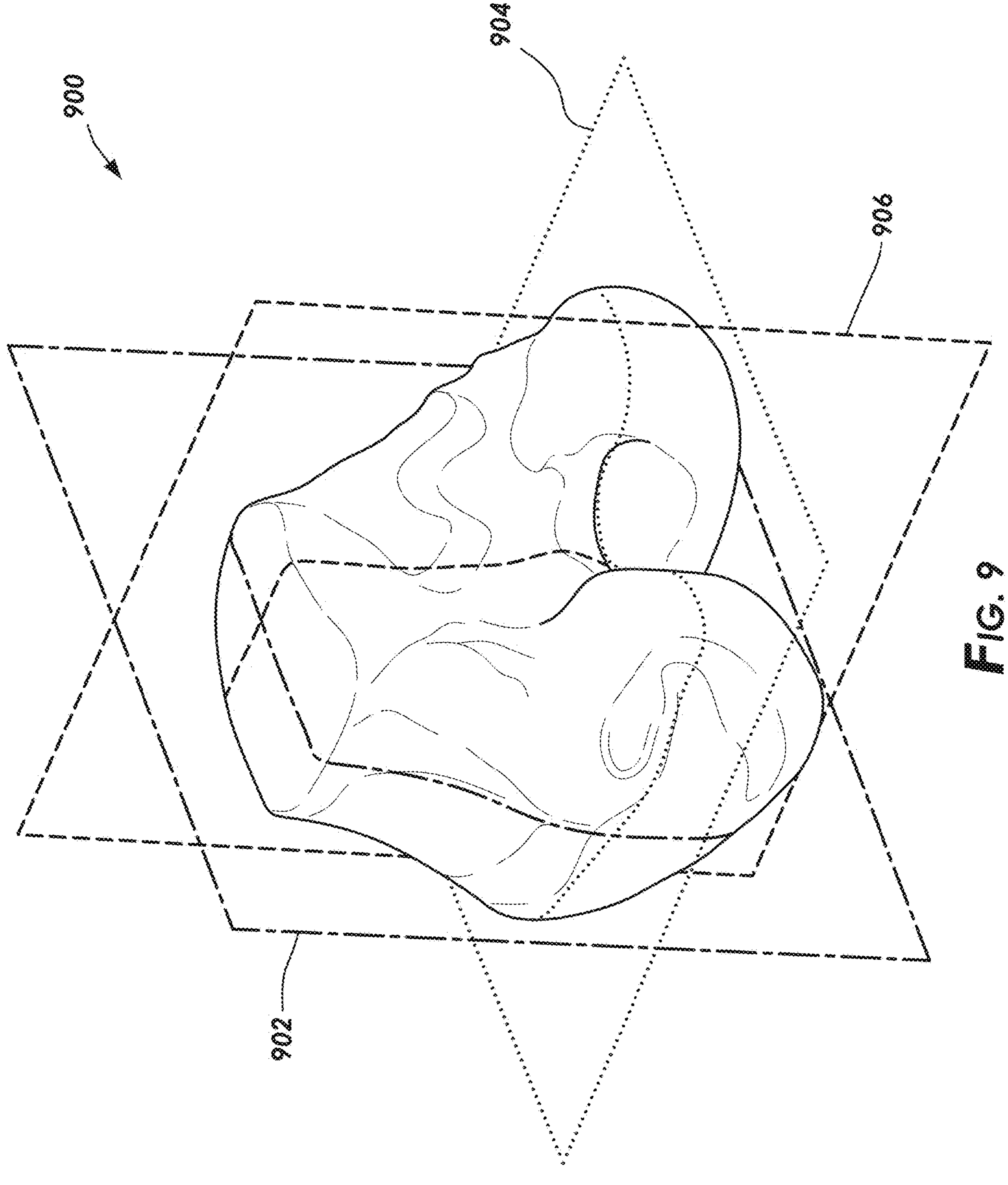
FIG. 9 depicts a non-limiting example embodiment of the disclosed technology according to some embodiments of the present disclosure.

Turning back to Process 300, Process 300 proceeds from Step 312 to Step 314 where engine 200 generates an ARF for the distal femur. As illustrated in FIG. 9, an example of a generated ARF 900 is depicted, which includes sagittal direction 906, axial direction 904 and coronal direction 902.

In Step 316, the generated ARF can be displayed as an overlay or part of the 3D model, which can be used for an ACL procedure, as discussed above. In some embodiments, the information related to the ARF, directions, BH grid and Blumensaat's line can be stored and utilized for subsequent ARF projections.

As such, based at least on the discussion above, the disclosed methodology, unlike conventional techniques, functions without requiring alignment with a template model, nor initialization of the sagittal direction. Indeed, the disclosed methodology can be performed without an entire femur model, and does not depend on the curvature pattern of the intercondylar contour. This, among other benefits, enables the disclosed methodology to be applicable to a wider variety of input models and different types of morphologies, and evidences a system that works in a more computationally efficient and accurate manner, while not being prone to suffer from local minima issues.

Reference Grid and Anatomical Reference for the Tibia

Figure 10A:
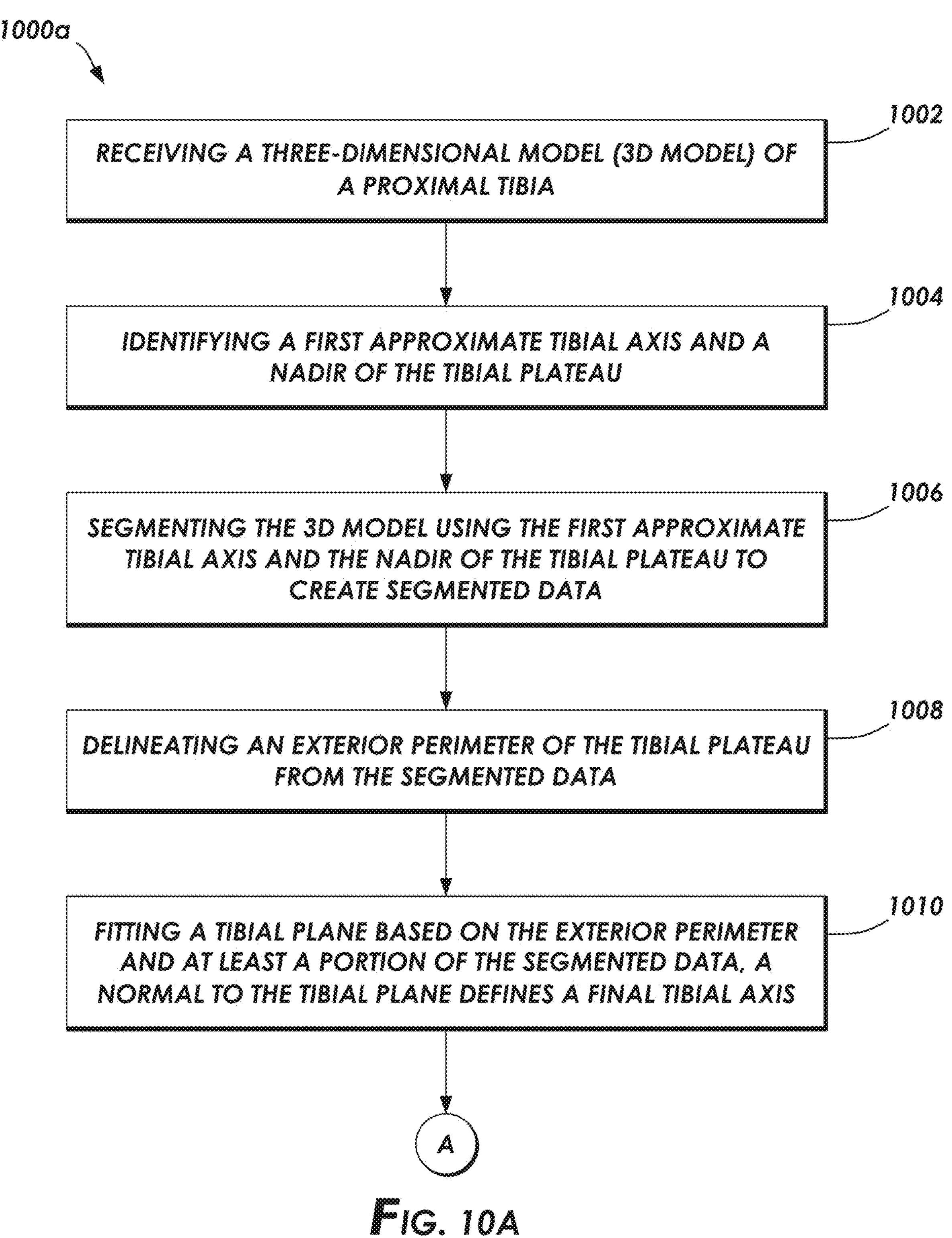
FIG. 10 (comprising FIGS. 10A and 10B) illustrates an exemplary data flow according to some embodiments of the present disclosure.
Figure 10B:
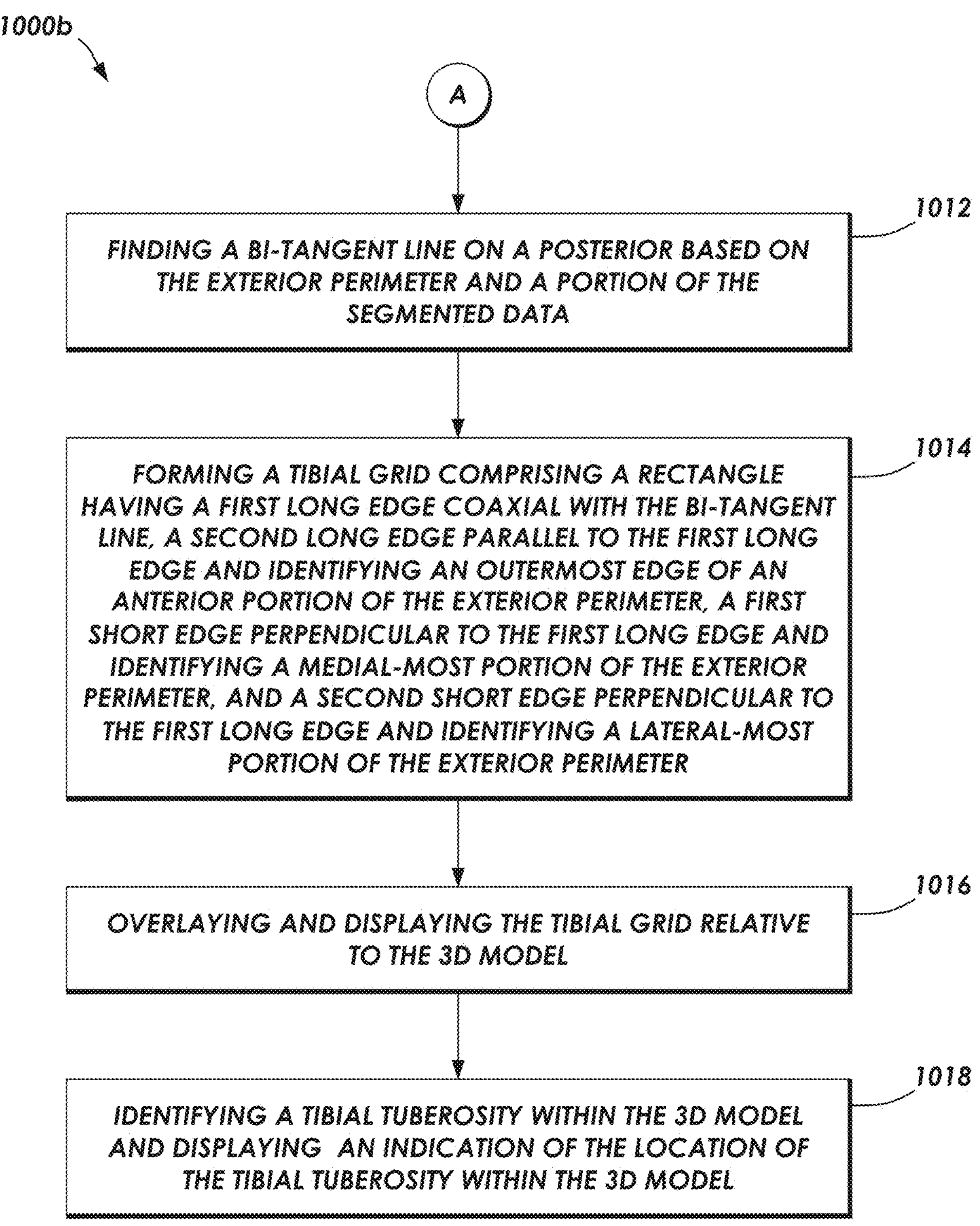

Turning to FIG. 10 (comprising FIGS. 10A and 10B), depicted is a Process 1000 which details non-limiting examples of the disclosed framework's computerized operations for placement of a tibial grid and determination an ARF.

According to some embodiments, as discussed herein, the framework (e.g., engine 200) can execute a methodology (as provided via at least Process 1000) that operates by determining the tibial plateau and the location of the tibial tuberosity. In particular, the methodology takes as input a 3D model of a proximal tibia and outputs a 3D axial direction, a rectangle enclosing the tibial plateau (e.g., a tibial grid) which directly provides estimations for the sagittal and coronal directions, and the location of the tibial tuberosity, all of which are computed in an automatic, unsupervised manner. The tibial grid can then be used by the surgeon to determine the ACL footprint using one of the numerous studies that provide this position in normalized coordinates, and the location of the tuberosity together with the axial direction can help the determination of the tunnel exterior orifice.

Given that the quadrant method is applied to the tibial plateau, in various examples the first steps consist of a rough and then a fine segmentation of the tibial plateau points. Robust plane fitting is then applied to determine the axial direction. From an axial view of the proximal tibia, the line that is bi-tangent to the posterior contour of the plateau is estimated and the parallel and perpendicular lines tangent to the posterior, medial and lateral plateau contours are then determined, providing the placement of the grid. The last step of the automatic algorithm consists in tibial tuberosity localization.

Tunnel entry points obtained with the method on 13 different femur models differ from the manual process by an average of 0.55 mm+0.35 mm. The error is about four times smaller than the smallest errors reported in the literature regarding related-art procedures. Concerning related-art semi-automatic grid placement algorithms, the disclosed approach also compares very favorably, presenting average errors in anterior-posterior and medial-lateral distances between automatic and manual placements of 0.63 mm instead of 2.4 mm, and 0.59 mm instead of 1.6 mm, respectively. The methodology disclosed herein is dependent upon neither user intervention, nor a large reconstruction of the tibial shaft, nor specific patient positioning during image acquisition, nor the availability of 3D models of other knee components, such as the patella. For these reasons, the disclosed methodology is applicable to a wider variety of input models.

The disclosed framework, realized via engine 200's execution of the operations detailed as part of Process 1000, is applicable to different tibia shapes and sizes, and its improved reliability, accuracy and ease of implementation can replace the related-art processing method upon which professionals currently rely.

According to some embodiments, Step 1002 of Process 1000 can be performed by the model module 202 of surgical engine 200; Steps 1004-1010 and 1018 can be performed by the estimation module 204; Steps 1010-1014 can be performed by placement module 206; and Step 1016 and a portion of Step 1018 can be performed by the display module 208.

Process 1000 begins with Step 302 where the engine 200 receives a 3D model of a proximal tibia. According to some embodiments, the receipt of the 3D model can be based on, but not limited to, a request to generate a 3D model, the search for and retrieval of a 3D model, and/or an upload and/or download of a 3D model. In some embodiments, the input can be in the form an image, message, multi-media item, and/or any other type of known or to be known format for engine 200 to receive and process for display a digital content corresponding to a model (e.g., 3D model) of a patient's bone, and particularly the proximal tibia. As before, while the discussion herein focuses on a 3D model of a proximal tibia, it should be construed as limiting, as other types, formats, and forms of models of other types of bones can be utilized without departing from the scope of the instant disclosure.

In Step 1004, engine 200 identifies a first approximate tibial axis and a deepest point of the tibial plateau (hereafter the nadir). In some examples, identifying the first approximate tibial axis and the nadir of the tibial plateau may involve morphing a statistical shape model (SSM) to correspond to the 3D model to create a morphed SSM, and identifying the first approximate tibial axis and the nadir of the tibial plateau from the morphed SSM. An SSM in this context is itself a three-dimensional model created based on a plurality of models of proximal tibias, the models statistically combined arrive at the SSM that represents a standard shape and size of the proximal tibia. The SSM has its tibial axis and nadir previously identified. "Morphing" in this instance may refer to adjusting or modifying the shape and/or scale of the SSM in a three dimensional coordinate system to correspond to the 3D model with a predetermined degree of certainty. Thus, in some examples the morphing may be an iterative process, morphing, checking correspondence, and repeating until the correspondence meets or exceeds the predetermined correspondence. The predetermined correspondence may be relatively low (e.g., 0.6 to 0.8), as the morphed SSM is used to merely find the first approximate tibial axis and nadir of the tibial plateau. By morphing the SSM to resemble the 3D model, an approximate axial direction of the 3D model is determined, as well as the nadir of the tibial plateau, the nadir disposed in medial plateau of the overall tibial plateau.

In yet still other examples, identifying the first approximate tibial axis and the nadir of the tibial plateau may involve use of a template model, an atlas, a deep learning framework, or the like. In still other examples, identifying the first approximate tibial axis may involve performing Principal Component Analysis (PCA) on the 3D model to determine the three most dominant, mutually orthogonal, directions. The three most dominant, mutually orthogonal, directions would thus corresponding to the three anatomical planes. Identifying the first approximate tibial axis and the nadir of the tibial plateau is discussed, with visual reference, in greater detail below.

In Step 1006, engine 200 segments the 3D model using the first approximate tibial axis and the nadir of the tibial plateau to create segmented data. In one example, segmenting the 3D model comprises selecting data points from the 3D model that reside in and above a segmentation plane, the segmentation plane perpendicular to the first approximate tibial axis, and the segmentation plane a predetermined distance below or distal of the nadir of the tibial plateau. Stated otherwise, from the first approximate tibial axis and the nadir, all the points that are above or proximal to a specified distance (e.g. 5 mm below or distal from the nadir) along the first approximate tibial axis are selected as the segmented data. In this way, the segmented data is highly likely to contain all the data points of the tibial plateau, but inasmuch as the segmentation is based on the first approximate tibial axis, additional data points will be present.

It is noted that segmenting may take many suitable forms. In some examples, the data that reside within and/or above the segmentation plane may be extracted and placed within new data file or a different memory location from non-segmented data. In other cases, however, the data that reside within and/or above the segmentation plane may be identified in some appropriate way within the 3D model, yet the 3D model may retain all the original data. Thus, segmentation may alternatively be referred to identifying data that reside within and/or above the segmentation plane, and should not be read to imply segregation of the data. Stated otherwise, segmented data need not be segregated data. Segmenting the 3D model using the first approximate tibial axis and the nadir of the tibial plateau to create segmented data is discussed, with visual reference, in greater detail below.

The rough segmentation resulting in the segmented data may include points that belong to the shaft of the tibia. In some cases, the segmented data may even contain points that belong to the fibula and should not be considered when placing the tibial grid. For this reason, the example methodology further refines the tibial plateau determination, as discussed in example Steps 1008 and 1010.

Thus, in Step 1008, engine 200 determines or delineates an exterior perimeter of the tibial plateau from within the segmented data. In one example, delineating the exterior perimeter of the tibial plateau comprises identifying contour regions within the segmented data, and assigning the exterior perimeter based on the contour regions. More particularly, in one example the refinement works by determining a 3D contour of and within the tibial plateau. In order to determine the 3D contour in this example, a filter with high response to regions of large 3D curvature is applied to the segmented data, and points having curvature at or above a predetermined value are specifically selected. In one example, a set of control points are selected using the morphed SSM, the control points being a set of high curvature points of the morphed SSM. The entire contour or exterior perimeter is then obtained by selecting the points of largest curvature within the segmented data that are not farther than a predetermined distance (e.g., 2 mm) from the control points. Stated otherwise, the exterior perimeter of the tibial plateau can be considered to be a line through a plurality of discrete data points residing on the selected points.

Thereafter, in one example, points inside the exterior perimeter are selected, such as by performing orthographic projection along the first approximate tibial axis. That is, the data points from the segmented data that reside within the exterior perimeter are identified, such as by orthographic projection, resulting in a set of data points comprising the data points of the exterior perimeter and at least a portion of the segmented data. Determining or delineating an exterior perimeter of the tibial plateau from within the segmented data is discussed, with visual reference, in greater detail below.

In Step 1010, engine 200 fits a tibial plane based on the exterior perimeter and at least a portion of the segmented data. A normal to the tibial plane defines a final tibial axis. In one example, given the exterior perimeter of the tibial plateau, and the portion of the segmented data that resides within the exterior perimeter, robust plane fitting is performed to determine a plane that contains at least some of the data points of the exterior perimeter and at least some of the segmented data. In some cases the 3D model of the tibial plateau may contain the tibial spines, and thus instead of considering all data points to fit a plane, the robust scheme may perform selection of inliers as part of plane-fitting process. The tibial plane so determined thus mathematically defines the "final" location of the tibial plateau, and the normal to the plane defines the final tibial axis. In one example, the "final tibial axis" is merely any line perpendicular to the tibial plateau, as the operative information is the direction, not the specific location of the tibial axis.

In another example, the tibial plane may be determined directly from the 3D model. That is, the example robust plane fitting may be performed on the entire 3D model as received in Step 1002. Any suitable plane-fitting algorithm may be used, such as voting schemes, Hough transforms, clustering, hypothesize-and-test algorithms, and the like. The example direct approach may thus obviate the use of the SSM to determine the first approximate tibial axis. In some cases, the PCA analysis discussed above may be used to restrict or limit the search and plane fitting with respect to the entire 3D model. When determining the tibial plane based on robust plane fitting performed on the 3D model, in whole or limited by the PCA analysis, the tibial plane so determined provides directly, via a normal to the tibial plane, the axial direction, and thus again this alternative obviates the need for use of the SSM to determine the first approximate tibial axis.

In yet still other examples, the tibial plane may be determined by plane fitting on just the data that define the exterior perimeter delineated in Step 1008, regardless of how identified. The data of the exterior perimeter may be used as the exclusive data set provided to the plane-fitting algorithm, and from which the tibial plane is determined. Any suitable plane-fitting algorithm may be used, such as voting schemes, Hough transforms, clustering, hypothesize-and-test algorithms, and the like.

Regardless of the precise methodology used to provide the tibial plane and the final tibial axis, the next step in the example methodology is placement of the tibial grid. Example Steps 1012 and 1014 perform the placement. In Step 1012, engine 200 finds a bi-tangent line at a posterior location based on the exterior perimeter and a portion of the segmented data. In one example, finding the bi-tangent line may comprise orthographically projecting the exterior perimeter and portions of the segmented data within the exterior perimeter onto the tibial plane to create projected data, and finding the bi-tangent on the posterior of the projected data.

That is, in order to determine the line that is bi-tangent to the posterior or posterior contour of the tibial plateau, the methodology projects onto the axial plane through orthographic projection. Then, the data points on the posterior side of the exterior perimeter are selected, in one example with the help of an approximate anterior-posterior direction retrieved using SSM. The posterior contour may then be divided into medial and lateral sides, and all lines containing one point from each side with equal tangents are generated. The line that is bi-tangent is selected as the line that makes all points reside on the line or reside on the same side of the line, and whose direction is equal to the direction of the tangents.

In Step 1014, engine 200 forms a tibial grid comprising a rectangle having a first long edge coincident or coaxial with the bi-tangent line, a second long edge parallel to the first long edge and identifying an outermost edge of an anterior of the exterior perimeter, a first short edge perpendicular to the first long edge and identifying a medial-most portion of the exterior perimeter, and a second short edge perpendicular to the first long edge and identifying a lateral-most portion of the exterior perimeter. From the correct placement of the tibial grid, the sagittal and coronal directions can be obtained as the directions of the long and short edges of the tibial grid, respectively. Forming the tibial grid is discussed, with visual reference, in greater detail below.

In the example above regarding Step 1012, the SSM is used to help determine the anterior-posterior direction. In example in which an SSM is not used, the anterior-posterior direction may be estimated based on the tibial spines. In particular, the tibial spines are the points of highest curvature in the segmented data, disposed near the centroid of the tibial plane, and the tibial spines belong to the posterior side. By algorithmically finding the tibial spines in the segmented data, or the 3D model directly, the anterior-posterior direction may be estimated. In yet still other examples, determining the medial-lateral direction, for placement of the bi-tangent, may be algorithmically determined by finding the side of the tibial plateau (e.g., based on the tibial plane) that contains more points with higher curvature. The side of the tibial plateau with more data points and higher curvature corresponds to the medial side.

In further examples, the bi-tangent may be determined without express identification of the medial and lateral directions. In particular, in the further example, the tangents of all the posterior points are determined. Using the tangents, some or all the possible tuples of the posterior points and corresponding tangents are established. The example then selects two tuples for which the two tangents and the line joining have the same direction. The example selects tuples that originate a line that does not cut through or resect the contour. And the bi-tangent is thus the line corresponding to the tuple with the largest distance between the points.

In Step 1016, engine 200 overlays and displays the tibial grid relative to the 3D model. That is, the surgeon may be provided a view of the tibia (e.g., along the final tibial axis) showing the tibial grid. The surgeon may select a tunnel aperture location on the tibial plateau based on the tibial grid.

Recent published articles consider the location of the tibial tuberosity for determining the exterior point of the ACL tibial tunnel. Due to the importance of this landmark, the methodology may further comprise automatic detection of the tibial tubercle or tibial tuberosity, which may be of help to the surgeon when deciding about the location of the tibial tunnel.

Thus, the example Process 1000 may also include Step 1018. In Step 1018, engine 200 identifies the tibial tuberosity within the 3D model and displays an indication of the location of the tibial tuberosity within the 3D model. In one example, identifying the tibial tuberosity may comprise projecting the 3D model onto a sagittal plane, segmenting the 3D model along a line perpendicular to the second long edge resulting in a tuberosity segmentation, and identifying an anterior-most portion of the tuberosity segmentation as the tibial tuberosity. By backprojecting onto 3D model, the center of the tuberosity is reconstructed. The ridge of the tubercle can be obtained as the intersection of the tubercle region with a plane whose normal is the sagittal direction and going through the most anterior point (center of the tuberosity).

In other examples, the orthographic projection and segmenting relative to the line perpendicular to the second long edge may be omitted, and instead curvature cues and/or a sphere may be fitted to the data from the 3D model to estimate the location of the tibial tuberosity. In yet still other cases, the location of the tibial tuberosity may be estimated using a template model, an atlas, a deep learning framework, or the like. The specification now turns to a visual explanation of the example methodology.

Figure 11:
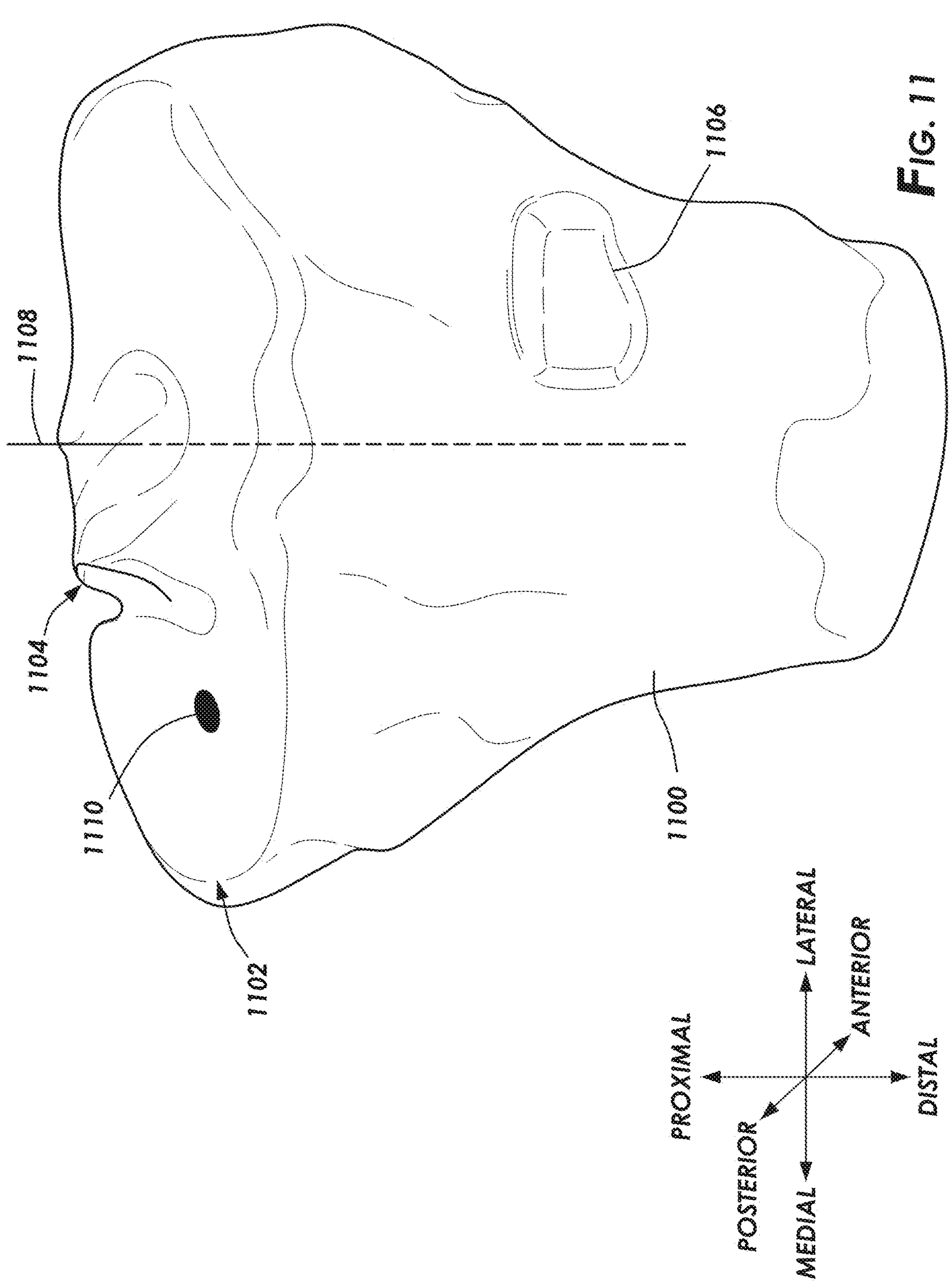
FIG. 11 shows a rendering of a 3D model of an example proximal tibia.

FIG. 11 shows a rendering of a 3D model of an example proximal tibia. In particular, visible in FIG. 11 is a portion of the tibia 1100, the tibial plateau 1102, the tibial spines 1104, the tibial tuberosity 1106, and the tibia axis 1108. On the medial side of the tibial plateau 1102 is the nadir 1110, again being the lowest or distal-most point of the tibial plateau 1102 (and more particularly, the medial plateau). The coordinate system of FIG. 11 shows the medial and lateral axis, the proximal and distal axis, and the anterior and posterior axis.

Figure 12:
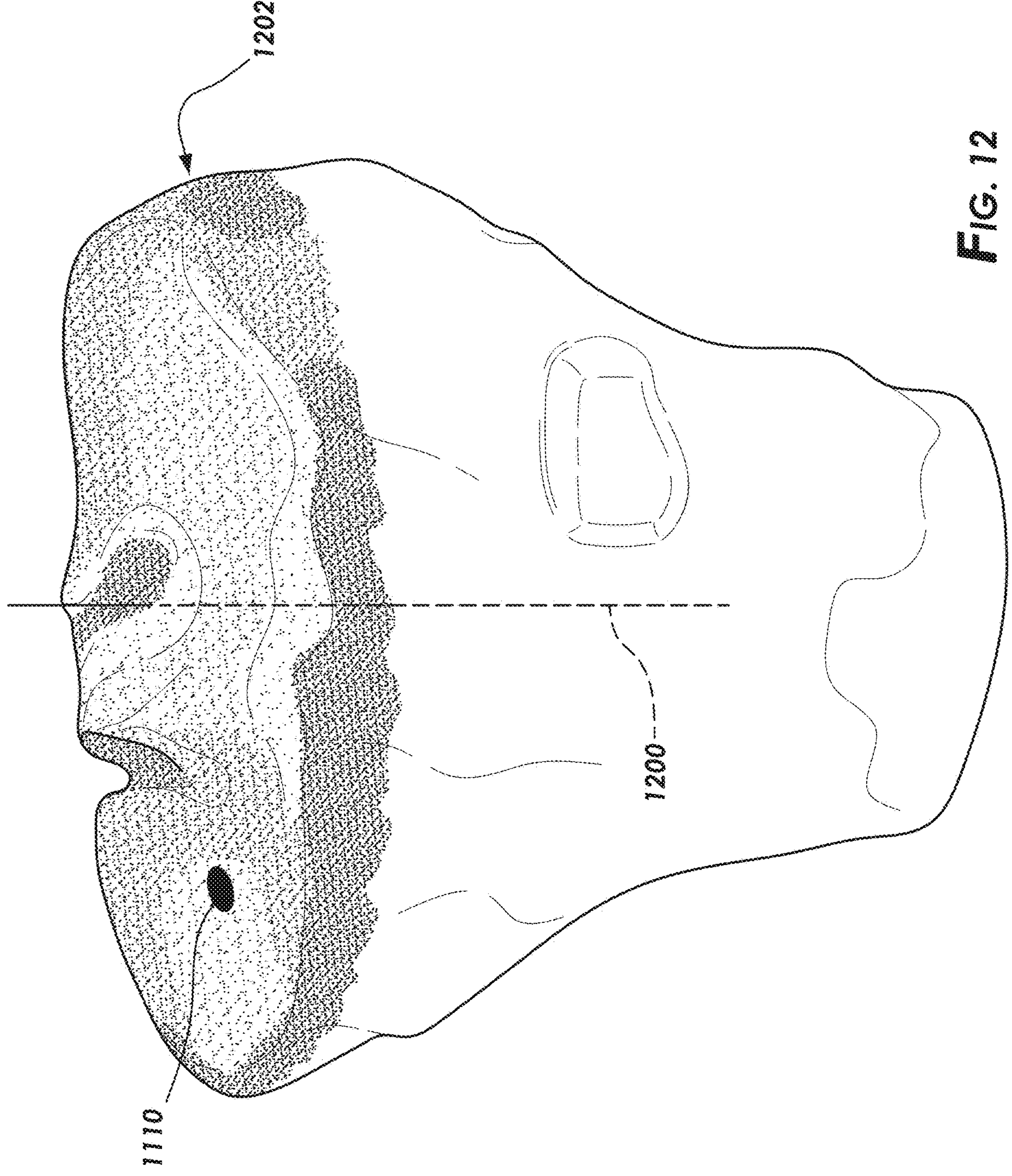
FIG. 12 shows a rendering of the 3D model showing the first approximate tibial axis and the nadir.

FIG. 12 shows a rendering of the 3D model showing the first approximate tibial axis 1200 and the nadir 1110. In the example methodology (e.g., Step 1004), a first approximate tibial axis 1200 and the nadir 1110 are determined, such as by morphing the SSM. However, any suitable technique may be used to find the first approximate tibial axis 1200 and the nadir 1110. In the example methodology, the data points are segmented by identifying all the data points of the 3D model that reside above a segmentation plane. The segmentation plane resides a predetermined distance below the nadir 1110 (e.g., 5 mm), and the segmentation plane is perpendicular to the first approximate tibial axis 1200. In FIG. 12, the segmented data 1202 are highlighted with stippling.

Figure 13:
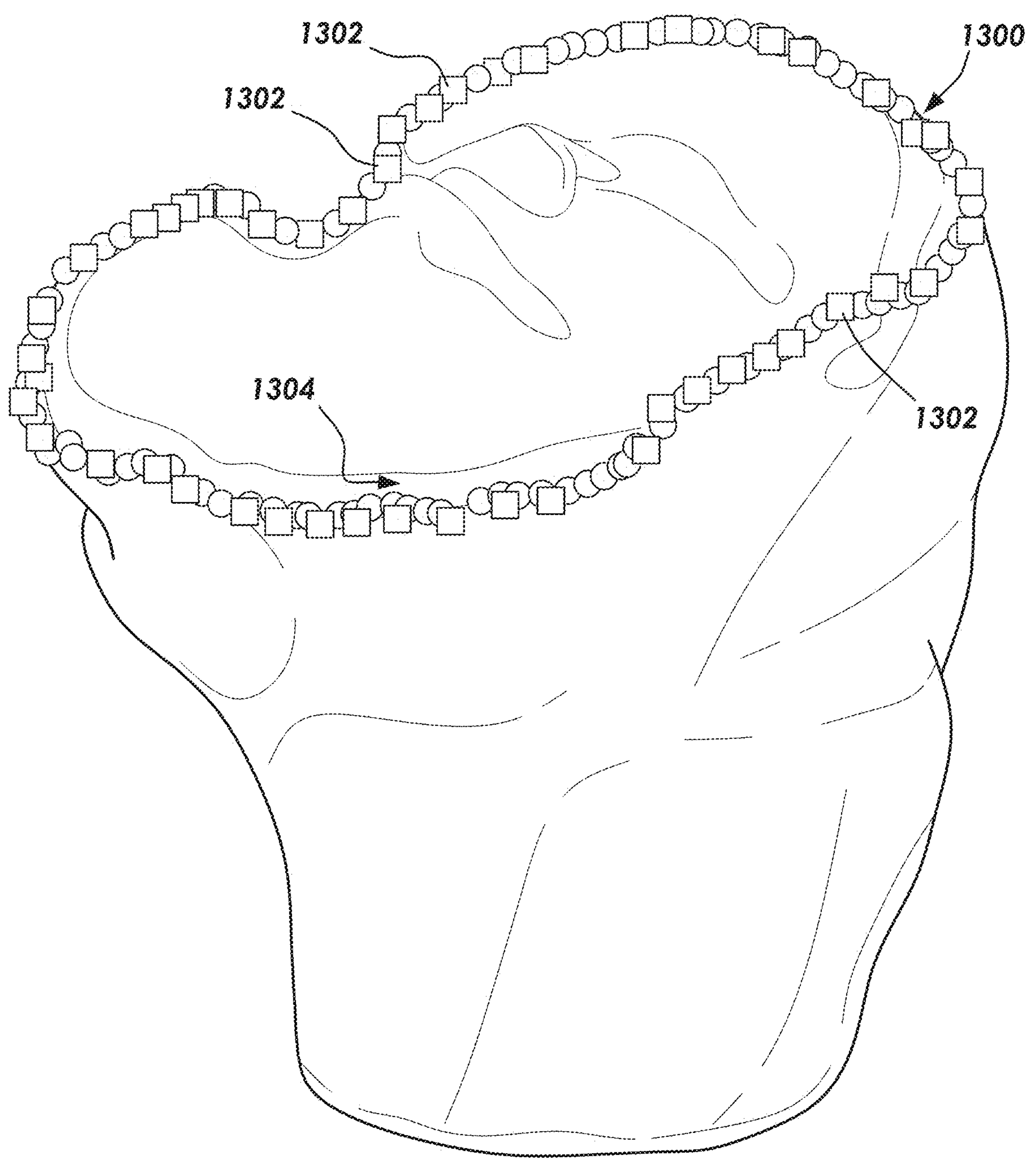
FIG. 13 shows a rendering of the 3D model including an example exterior perimeter.

FIG. 13 shows a rendering of the 3D model including an example exterior perimeter 1300. In the example methodology (e.g., Step 1008), the segmented data are refined to better delineate the exterior perimeter of the tibial plateau. In one example, the morphed SSM defines a control set or an initial set of perimeter data points of the tibial plateau, the initial set of perimeter data points 1302 illustrated as squares, only some of which are associated with reference numbers. Moreover, the segmented data are subjected to an algorithm that identifies high-contour regions. The high contour regions, such as region 1304, are connected up with the initial set of perimeter data points 1302 to define the external perimeter 1300 (combination of squares and circles). The data points of the external perimeter 1300, and the data points that reside within the exterior perimeter, thus may be considered the detailed or fine segmentation.

Figure 14:
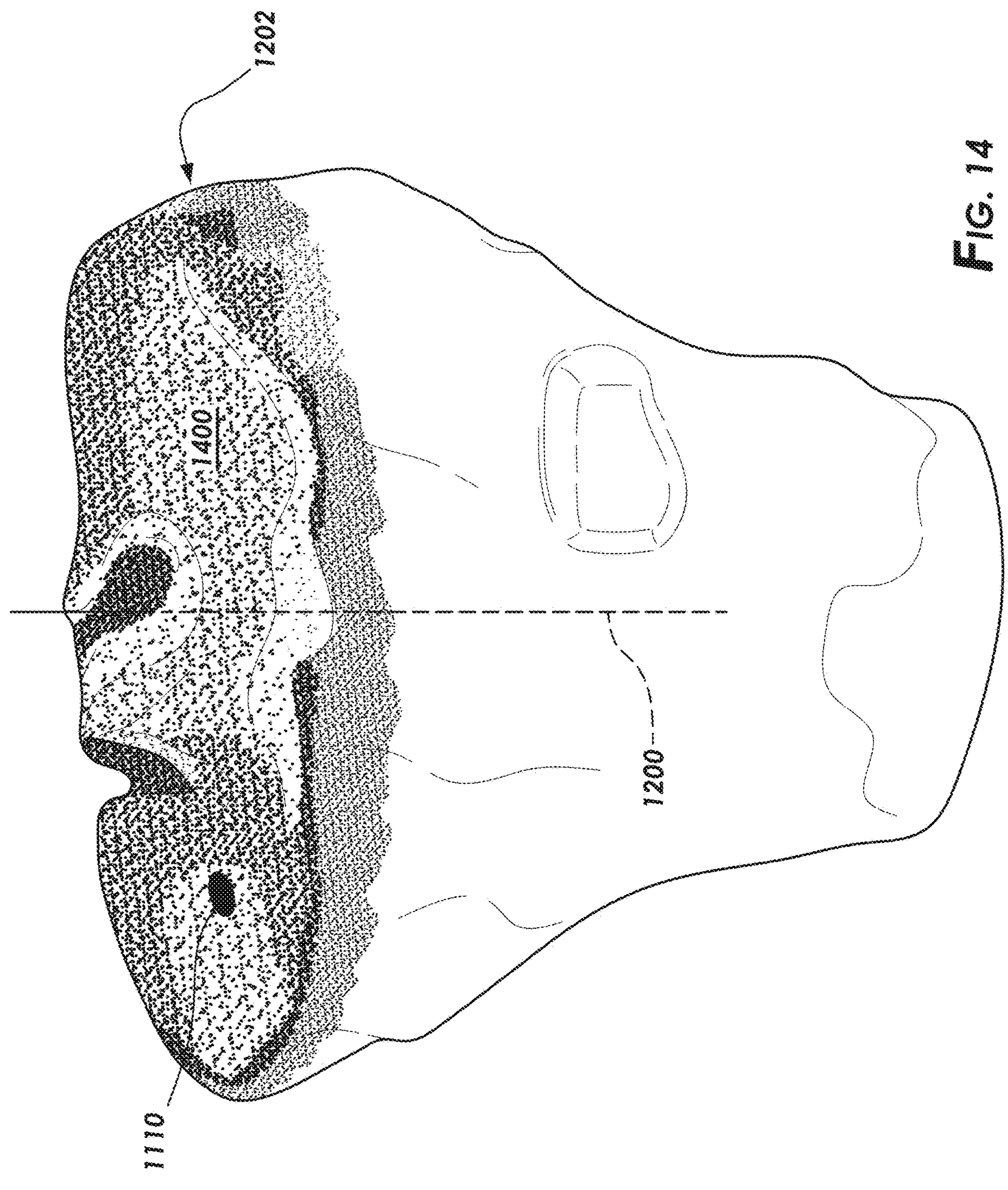
FIG. 14 shows a rendering of the 3D model highlighting the exterior perimeter and portion of the segmented data.

FIG. 14 shows a rendering of the 3D model highlighting the segmented data, the exterior perimeter, and portion of the segmented data that resides within the exterior perimeter. In particular, visible in FIG. 14 are the segmented data 1202, the first approximate tibial axis 1200, and the nadir 1110. Within the segmented data 1202, the data points defining the exterior perimeter and the data points of the segmented data that reside within the exterior perimeter, region 1400.

Figures 15, 16:
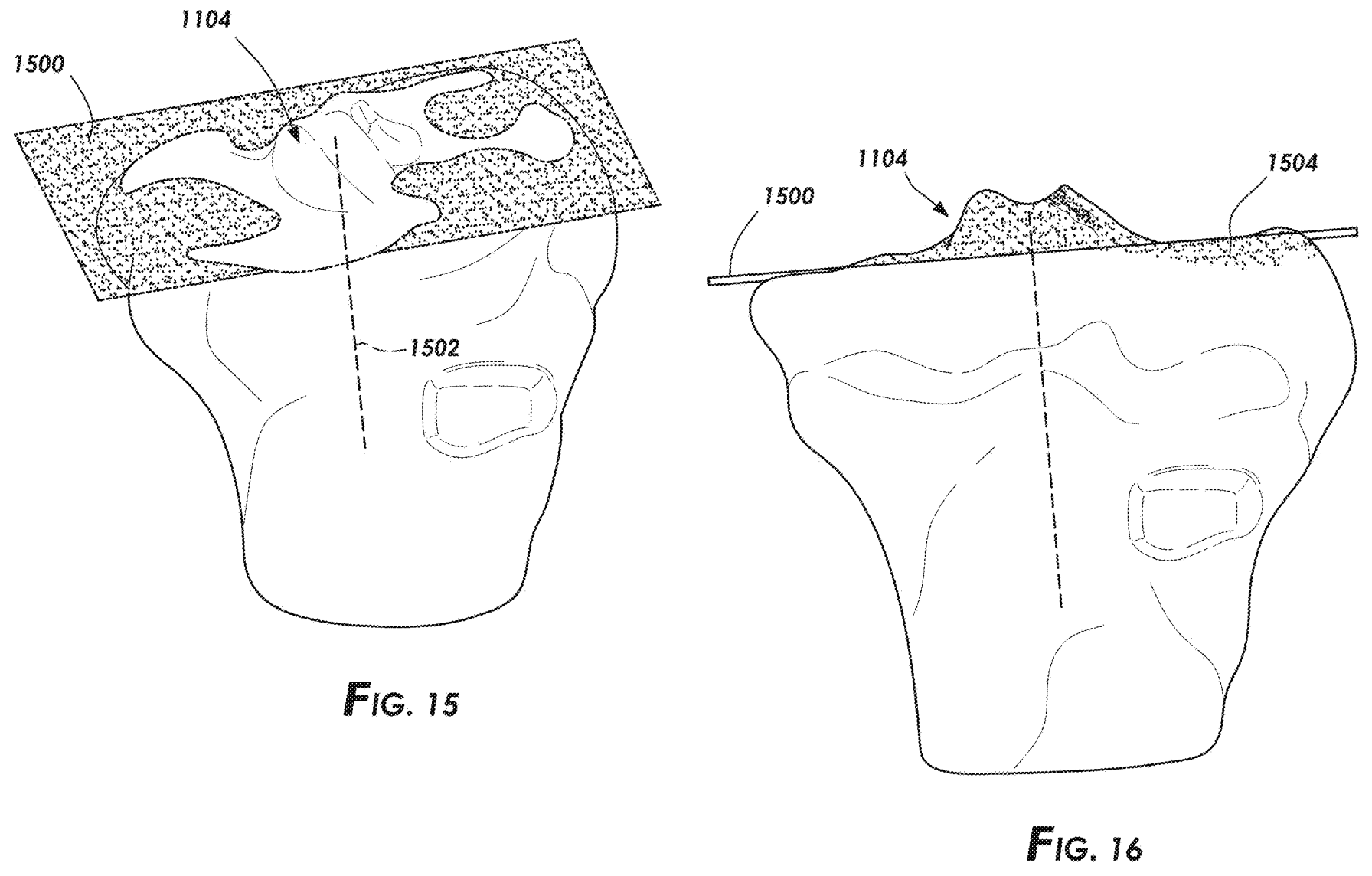

FIG. 15 shows a perspective view of a rendering of the 3D model including a tibial plane. In the example methodology (e.g., Step 1010), the data points defining the exterior perimeter, and the data points of the segmented data that reside within the exterior perimeter, are subjected to a plane-fitting algorithm to find a good-fit mathematical plane, such as tibial plane 1500. It is noted that not all the data points of the exterior perimeter and/or the data points of the segmented data that reside within the exterior perimeter reside within the tibial plane 1500. Once the tibial plane 1500 is determined, a line perpendicular to the tibial plane 1500 defines the final tibial axis 1502. Notice the tibial spines 1104 that, while residing within the exterior perimeter (not specifically delineated in FIG. 15), rise above the tibial plane 1500, and define and reside within the posterior portion of the tibial plane 1500.

FIG. 16 shows a side elevation view of a rendering of the 3D model including the tibial plane. FIG. 16 better shows the normal or perpendicular relationship of the final tibial axis 1502 to the tibial plane 1500. Moreover, the view of FIG. 16 shows how portions of the data that otherwise resides within the exterior perimeter nevertheless may rise above (e.g., the tibial spines 1104) or fall below (e.g., the lateral condyle 1504) the tibial plane 1500.

Figure 17:
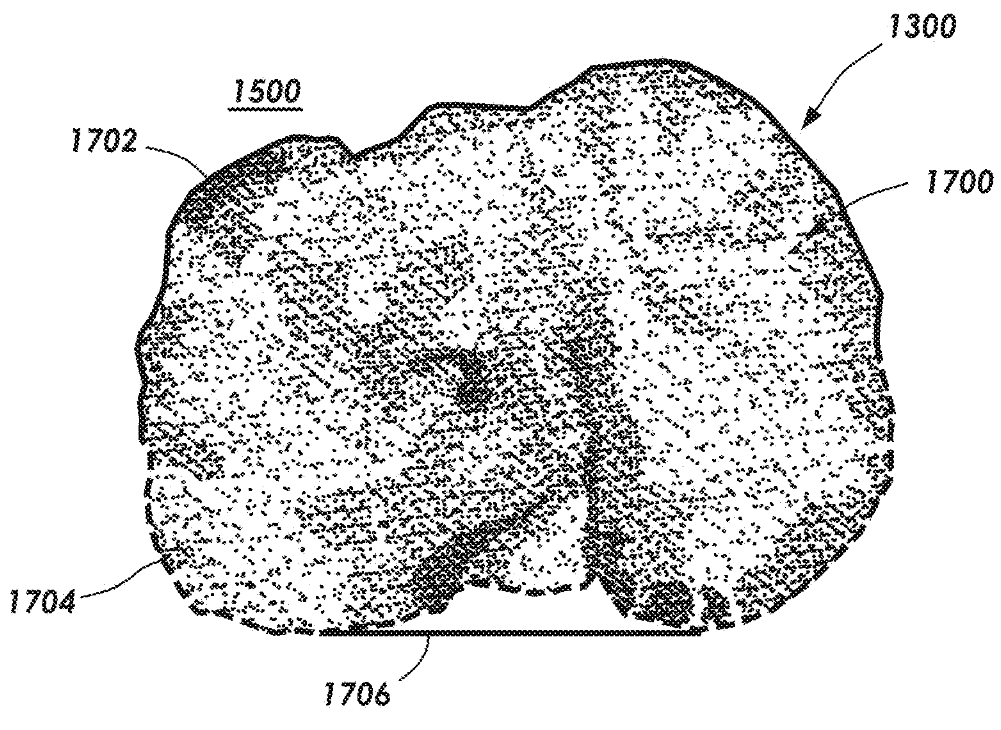
FIG. 17 shows a projection of the data points of the exterior perimeter, and the data points that reside within the exterior perimeter, projected onto the final tibial plane, along with the bi-tangent line.

FIG. 17 shows the data points of the exterior perimeter, and the data points that reside within the exterior perimeter, projected onto the tibial plane, along with the bi-tangent line. In the example methodology (e.g., Step 1012), the data points of the exterior perimeter 1300 and the data that reside within the exterior perimeter (points 1700) may be orthographically projected onto a plane perpendicular to the final tibial axis 1502, such as the tibial plane 1500 itself (e.g., the plane of the page). The anterior portion 1702 of the projection and the posterior portion 1704 may be determined in any suitable form, such as by using the SSM or by way of the tibial spines. With the posterior portion 1704 determined, a bi-tangent line 1706 may be placed, as discussed in detail above. The bi-tangent line 1706 defines a line that resides within the coronal plane. A line perpendicular to the final tibial axis 1502 and perpendicular the bi-tangent line 1706 may define the coronal direction.

Figure 18:
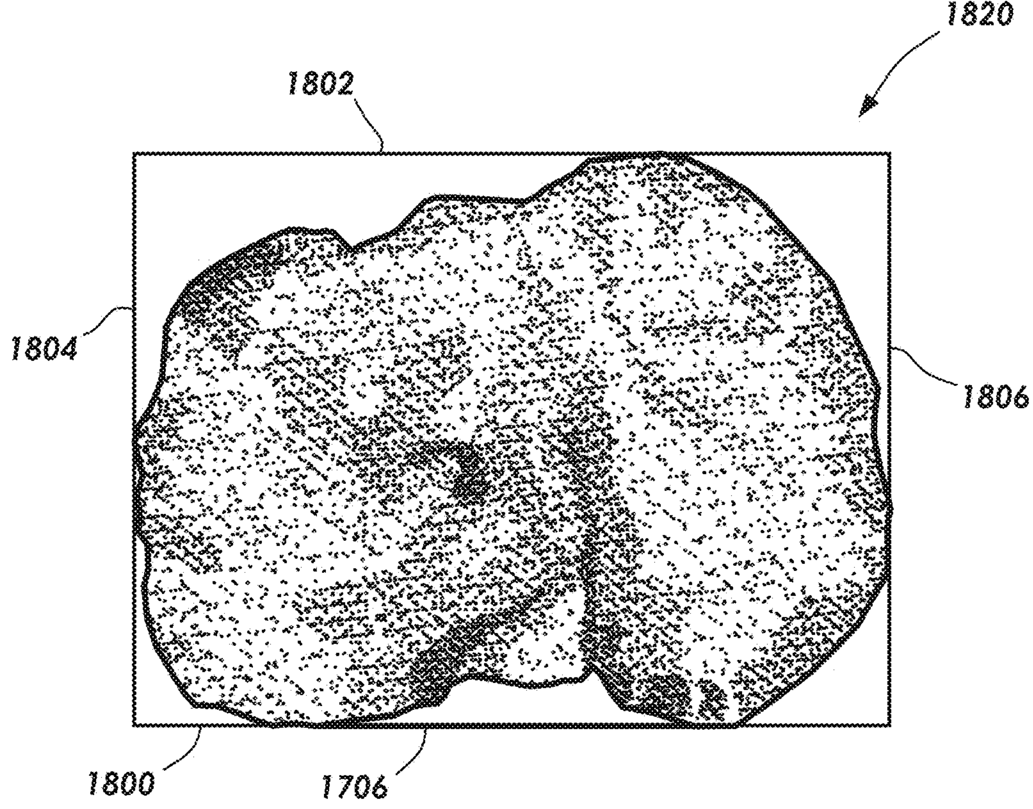
FIG. 18 shows the projection of FIG. 17 with tibial grid disposed thereon.

FIG. 18 shows the projection of FIG. 17 with tibial grid disposed thereon. In the example methodology (e.g., Step 1014), disposing the tibial grid may involve fitting or finding a smallest rectangle around the projected data points, the rectangle having a first long edge 1800 coaxial with the bi-tangent line 1706, a second long edge 1802 parallel to the bi-tangent line 1706, and two short edges 1804 and 1806 that are parallel to each other and perpendicular the long edges 1800 and 1802. The short edges 1804 and/or 1806 thus define the coronal direction. The rectangle formed by edges 1800, 1802, 1804, and 1806 may be considered to define the tibial grid 1820 with an origin or location (0%, 0%) at the lower left of FIG. 18, and (100%, 100%) at the upper right. The tibial grid 1820 can then be used by the surgeon to determine the ACL footprint using one of the numerous studies that provide the position in normalized coordinates.

Figure 19:
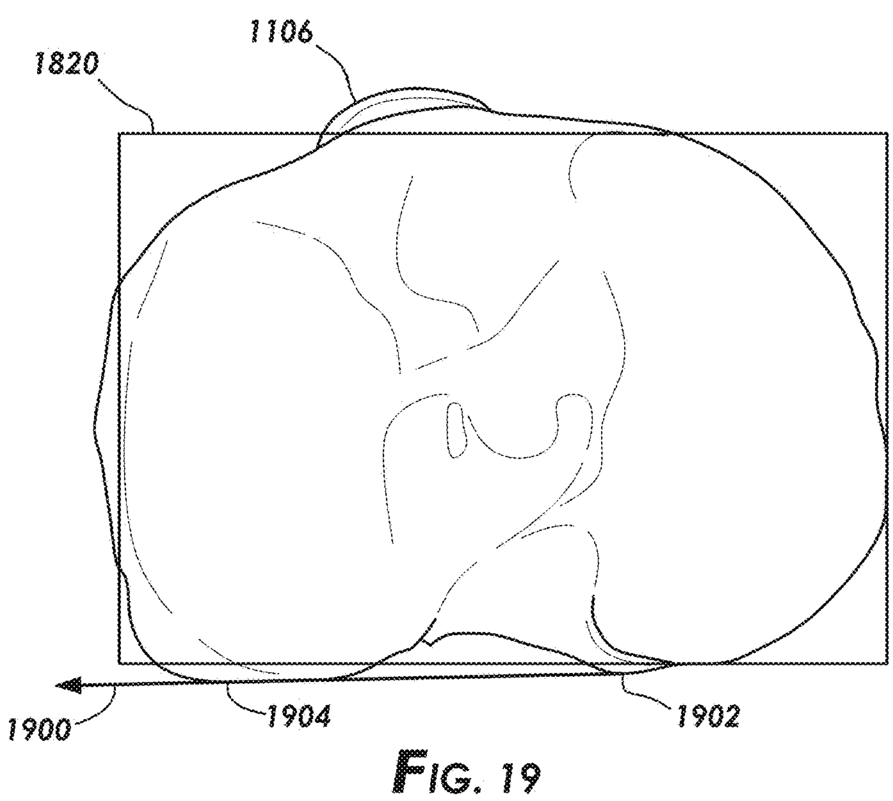
FIG. 19 shows an axial view of the rendering of the 3D model including the tibial grid.

FIG. 19 shows an axial view of the rendering of the 3D model including the tibial grid. In the example methodology (e.g., Step 1016), the tibial grid 1820 determined as discussed above may be overlaid and displayed, such as on a computer screen within the surgical setting, such that the surgeon can select the aperture location for the tibial tunnel on the tibial plateau. Notice the location of the tibial tuberosity 1106.

In yet still further examples, the sagittal direction may be estimated as the direction of a line that goes through the most posterior lateral and medial points of the orthographic projecting in the axial direction. For example, in the view of FIG. 19, the sagittal direction may be considered line 1900 intersecting the most posterior lateral point 1902 and the most posterior medial point 1904. It is noted that the sagittal direction determined according to most posterior lateral and medial points may differ slightly from a sagittal direction determined as coincident with the bi-tangent.

Figure 20:
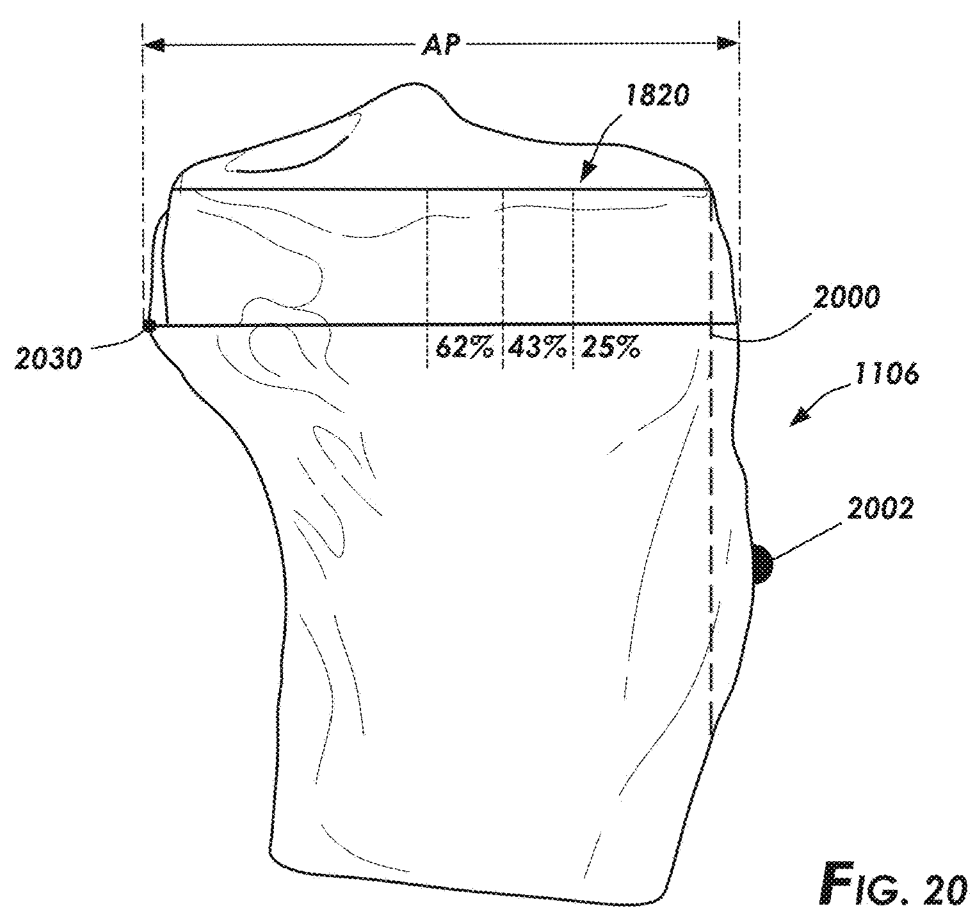
FIG. 20 shows side elevation view of the rendering of the 3D model including a tibial plane.

FIG. 20 shows a sagittal or side elevation view of the rendering of the 3D model including a tibial plane. In the example methodology (e.g., Step 1018), the tibial tuberosity 1106 may be programmatically determined by projecting the 3D model in the sagittal direction as shown in FIG. 20, narrowing or segmenting data points that reside anterior to a segmentation line 2000, where the segmentation line 2000 is parallel to the final tibial axis (not specifically shown), and the segmentation line 2000 intersects the anterior long edge 1802 of the tibial grid 1808. The tibial tuberosity 1106 may thus be programmatically determined as the maxima or apex (e.g., the anterior-most point 2002) of the segmented data points. With the tibial grid 1820 programmatically placed, and the tibial tuberosity 1106 programmatically determined, the clinician may plan the tibial tunnel locations, and send the information to the intraoperative equipment.

Still referring to FIG. 20. In order to further assist the surgeon in placement of the tibial tunnel, and in further examples, additional scale invariant information may be generated. In particular, with the 3D model projected in the sagittal direction as shown in FIG. 20, further examples find the posterior-most point 2030. The posterior-most point 2030, and a line 2032 parallel to the tibial grid 1820, together define an anterior-posterior distant (AP in the figure, and hereafter AP distance). The AP distance may be delineated as shown in FIG. 20, such as at the 25% of the AP distance, 43% of the AP distance, and 62% of the AP distance. These delineations may be helpful in determining placement of the tibial tunnel, or at least the location of the aperture of tibial tunnel on the tibial plateau.

In examples discussed above, the segmentation plane was selected as a plane perpendicular to the first approximate tibial axis at a predetermined distance below or distal to the nadir 1110 (FIG. 11). In other examples, however, the segmentation plane may be based on the posterior-most point 2030 of the tibia. In particular, in these examples a sagittal direction may be estimated in any suitable form, such as using the sagittal direction determined from the analysis of the 3D model of the femur from the same patient (the imaging taken with the patient's leg in extension). With the estimated sagittal direction, the 3D model may be projected as shown in FIG. 20, and the posterior-most point 2030 determined. Using the posterior-most point 2030, the segmentation plane may again be a plane perpendicular to the first approximate tibial axis and containing the posterior-most point 2030. In other cases, the segmentation plane may be at a predetermined distance below or distal to the posterior-most point 2030 (e.g., 3 mm), and again the segmentation plane perpendicular to the first approximate tibial axis. With segmented data determined based on the alternate segmentation plane, the various example steps discussed above may be used to place the tibial grid.

Figure 21:
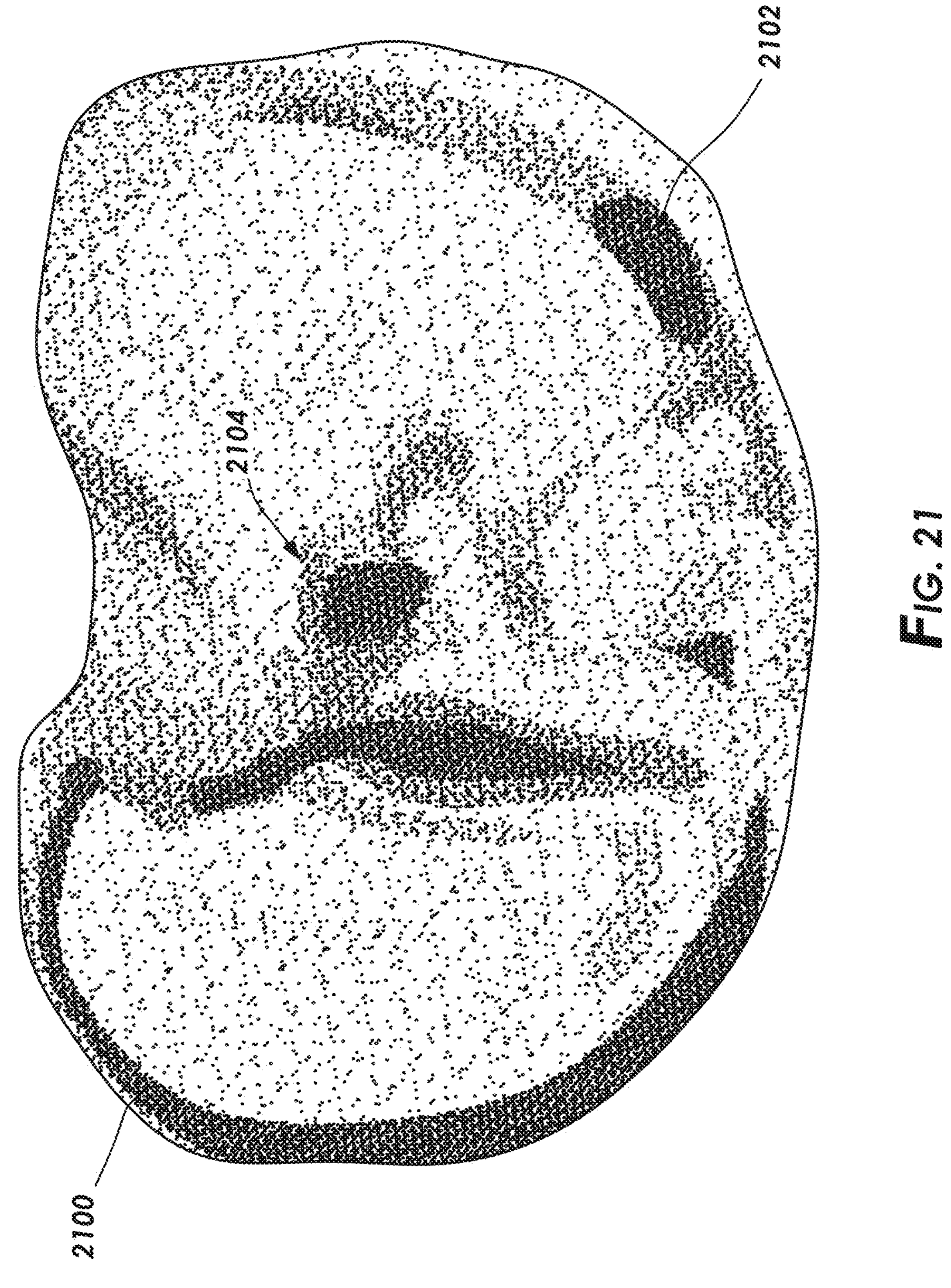
FIG. 21 shows a rendering of the 3D curvature values projected onto an axial plane.

FIG. 21 shows a rendering of the 3D curvature values projected onto an axial plane. As mentioned above, in alternative embodiments the tibial plateau may be determined without the use of prior information, such as the SSM. In particular, in alternative embodiments the 3D model, or at least the segmented data of the 3D model, may be evaluated to determine 3D curvature values, such as areas 2100, 2102, and at the location of the tibial spines in area 2104. The 3D curvature values may be used to generate a two-dimensional image by projecting the 3D curvature values onto an axial plane, the projection as illustrated in FIG. 21. Any suitable morphologic operation may be applied to the 2D projection to find a closed contour, where the closed contour thus defines the exterior perimeter. If needed, the data defining the exterior perimeter may then be back projected to the segmented data to identify the portion of the segmented data that resides within the exterior perimeter.

Figure 22:
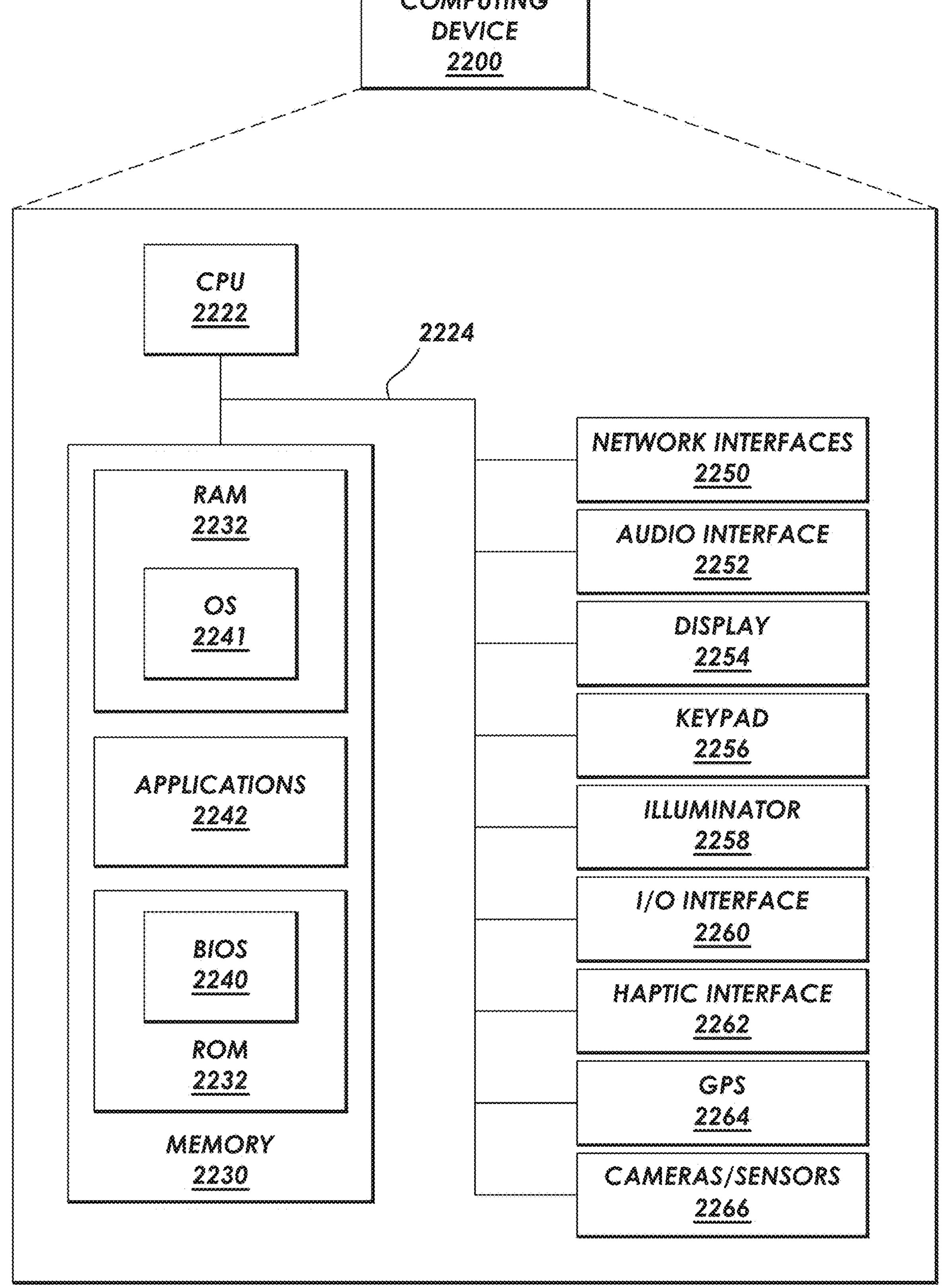
FIG. 22 is a block diagram illustrating a computing device showing an example of a device used in various embodiments of the present disclosure.

FIG. 22 is a block diagram illustrating a computing device 2200 (e.g., UE 106, as discussed above) showing an example of a client device or server device used in the various embodiments of the disclosure.

The computing device 2200 may include more or fewer components than those shown in FIG. 22, depending on the deployment or usage of the device 2200. For example, a server computing device, such as a rack-mounted server, may not include audio interfaces 2252, displays 2254, keypads 2256, illuminators 2258, haptic interfaces 2262, GPS receivers 2264, or cameras/sensors 2266. Some devices may include additional components not shown, such as GPU devices, cryptographic co-processors, AI accelerators, or other peripheral devices.

As shown in FIG. 22, the device 2200 includes a central processing unit (CPU) 2222 in communication with a mass memory 2230 via a bus 2224. The computing device 2200 also includes one or more network interfaces 2250, an audio interface 2252, a display 2254, a keypad 2256, an illuminator 2258, an input/output interface 2260, a haptic interface 2262, an optional GPS receiver 2264 (and/or an interchangeable or additional GNSS receiver) and a camera(s) or other optical, thermal, or electromagnetic sensors 2266. Device 2200 can include one camera/sensor 2266 or a plurality of cameras/sensors 2266. The positioning of the camera(s)/sensor(s) 2266 on the device 2200 can change per device 2200 model, per device 2200 capabilities, and the like, or some combination thereof.

In some embodiments, the CPU 2222 may comprise a general-purpose CPU. The CPU 2222 may comprise a single-core or multiple-core CPU. The CPU 2222 may comprise a system-on-a-chip (SoC) or a similar embedded system. In some embodiments, a GPU may be used in place of, or in combination with, a CPU 2222. Mass memory 2230 may comprise a dynamic random-access memory (DRAM) device, a static random-access memory device (SRAM), or a Flash (e.g., NAND Flash) memory device. In some embodiments, mass memory 2230 may comprise a combination of such memory types. In one embodiment, the bus 2224 may comprise a Peripheral Component Interconnect Express (PCIe) bus. In some embodiments, the bus 2224 may comprise multiple busses instead of a single bus.

Mass memory 2230 illustrates another example of computer storage media for the storage of information such as computer-readable instructions, data structures, program modules, or other data. Mass memory 2230 stores a basic input/output system ("BIOS") 2240 for controlling the low-level operation of the computing device 2200. The mass memory also stores an operating system 2241 for controlling the operation of the computing device 2200.

Applications 2242 may include computer-executable instructions which, when executed by the computing device 2200, perform any of the methods (or portions of the methods) described previously in the description of the preceding Figures. In some embodiments, the software or programs implementing the method embodiments can be read from a hard disk drive (not illustrated) and temporarily stored in RAM 2232 by CPU 2222. CPU 2222 may then read the software or data from RAM 2232, process them, and store them to RAM 2232 again.

The computing device 2200 may optionally communicate with a base station (not shown) or directly with another computing device. Network interface 2250 is sometimes known as a transceiver, transceiving device, or network interface card (NIC).

The audio interface 2252 produces and receives audio signals such as the sound of a human voice. For example, the audio interface 2252 may be coupled to a speaker and microphone (not shown) to enable telecommunication with others or generate an audio acknowledgment for some action. Display 2254 may be a liquid crystal display (LCD), gas plasma, light-emitting diode (LED), or any other type of display used with a computing device. Display 2254 may also include a touch-sensitive screen arranged to receive input from an object such as a stylus or a digit from a human hand.

Keypad 2256 may comprise any input device arranged to receive input from a user. Illuminator 2258 may provide a status indication or provide light.

The computing device 2200 also comprises an input/output interface 2260 for communicating with external devices, using communication technologies, such as USB, infrared, Bluetooth™, or the like. The haptic interface 2262 provides tactile feedback to a user of the client device.

The GPS transceiver 2264 can determine the physical coordinates of the computing device 2200 on the surface of the Earth, which typically outputs a location as latitude and longitude values. GPS transceiver 2264 can also employ other geo-positioning mechanisms, including, but not limited to, triangulation, assisted GPS (AGPS), E-OTD, CI, SAI, ETA, BSS, or the like, to further determine the physical location of the computing device 2200 on the surface of the Earth. In one embodiment, however, the computing device 2200 may communicate through other components, provide other information that may be employed to determine a physical location of the device, including, for example, a MAC address, IP address, or the like.

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module may be stored on a computer readable medium for execution by a processor. Modules may be integral to one or more servers, or be loaded and executed by one or more servers. One or more modules may be grouped into an engine or an application.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

The following clauses define various non-limiting examples.

Clause 1. A computer-implemented method comprising: identifying, by a device, a three-dimensional (3D) model of a femur; analyzing, by a device, the 3D model, and determining a pair of points on the femur that have normal vectors that are orthogonal to a vector joining the pair of points; analyzing, by a device, the vector, and determining a sagittal direction; further analyzing, by the device, the 3D model based on the determined sagittal direction, and generating an intersection map of the 3D model, the intersection map comprising information related to a curve value of an intercondylar region; determining, by a device, a Blumensaat line based on the intersection map; analyzing, by the device, the intersection map in accordance with the Blumensaat line, and determining a Bernard-Hertel (BH) grid, the BH grid comprising an area that encloses condyles when the femur is subject to a lateral view; and placing, by a device, a digital representation of the BH grid as an overlay of the 3D model.

Clause 2. The computer-implemented method of clause 1, further comprising: determining values for the pair of points and each normal vector; clustering the determined values; and determining a median value based on the clustering, wherein the determined sagittal direction corresponds to the median value.

Clause 3. The computer-implemented method of any preceding clause, further comprising: executing, by a device, an estimation model; and determining the sagittal direction based on an output of the estimation model.

Clause 4. The computer-implemented method of any preceding clause, further comprising: identifying lateral and medial condyles; and determining, based on the identified lateral and medial condyles, a lateral-medial orientation of the sagittal direction.

Clause 5. The computer-implemented method of clause 4, further comprising refining the sagittal direction based on adjustments of an outer border of the lateral and medial condyles.

Clause 6. The computer-implemented method of any preceding clause, further comprising backprojecting the BH grid to the 3D model, the BH grid being a two-dimensional (2D) model, wherein the backprojection is based on a sectioning plane defined by the sagittal direction and Blumensaat's line.

Clause 7. The computer-implemented method of any preceding clause, further comprising: backprojecting points on the intersection map to points on the 3D model, wherein the points on the intersection map are two-dimensional (2D); and obtaining a sectioning plane of the 3D model based on the sagittal direction; and determining an axial direction via circle fitting.

Clause 8. The computer-implemented method of any preceding clause, further comprising: determining contours of the femur based on a sagittal view of the femur, the sagittal view being obtained through 2D projection along the sagittal direction; searching for circles that are tangent to the contours in two points; and estimating a line that joins respective centers of the circles, wherein the estimated line provides information related to an axial direction.

Clause 9. The computer-implemented method of any preceding clause, further comprising: analyzing, based on the sagittal direction, the femur, and determining a sagittal view of the femur; determining, based on the sagittal view, an axial direction; and determining a coronal direction based on a cross-product of the sagittal and axial directions.

Clause 10. The computer-implemented method of clause 9, further comprising determining an anatomical reference frame (ARF) of the femur based on the sagittal, axial and coronal directions.

Clause 11. The computer-implemented method of any preceding clause, further comprising: identifying an orthographic projection of the femur; identifying, based on the orthographic projection, a set of projection rays within the 3D model related to the femur; determining a set of intersections corresponding to the set of projection rays, wherein the intersection map comprises information related to the set of intersections.

Clause 12. The computer-implemented method of clause 12, further comprising: analyzing, via edge detection analysis, the set of intersections; and determining the curve value of the intercondylar region based on the edge detection analysis, wherein the Blumensaat line is tangential to a curve associated with the curve value.

Clause 13. A non-transitory computer-readable storage medium tangibly encoded with computer-executable instructions, that when executed by one or more devices, cause the one or more devices to: identify a three-dimensional (3D) model of a femur; analyzing the 3D model, and determine a pair of points on the femur that have normal vectors that are orthogonal to a vector joining the pair of points; analyze the vector, and determine a sagittal direction; further analyze the 3D model based on the sagittal direction, and generate an intersection map of the 3D model, the intersection map comprising information related to a curve value of an intercondylar region; determine a Blumensaat line based on the intersection map; analyze the intersection map in accordance with the Blumensaat line, and determine a Bernard-Hertel (BH) grid, the BH grid comprising an area that encloses condyles when the femur is subject to a lateral view; and place a digital representation of the BH grid as an overlay of the 3D model.

Clause 14. The non-transitory computer-readable storage medium of clause 13, wherein the instructions further cause the one or more devices to: determine values for the pair of points and each normal vector; cluster the values; and determine a median value based on the clustering, wherein the sagittal direction corresponds to the median value.

Clause 15. The non-transitory computer-readable storage medium of any of clauses 13-14, wherein the instructions further cause the one or more devices to: identify lateral and medial condyles; determine, based on the identified lateral and medial condyles, a lateral-medial orientation of the sagittal direction; and refine the sagittal direction based on adjustments of an outer border of the lateral and medial condyles.

Clause 16. The non-transitory computer-readable storage medium of any of clauses 13-15, wherein the instructions further cause the one or more devices to: backproject points on the intersection map to points on the 3D model, wherein the points on the intersection map are two-dimensional (2D); obtain a sectioning plane of the 3D model based on the sagittal direction; and determine an axial direction via circle fitting.

Clause 17. The non-transitory computer-readable storage medium of any of clauses 13-16, wherein the instructions further cause the one or more devices to: determine contours of the femur based on a sagittal view of the femur, the sagittal view being obtained through 2D projection along the sagittal direction; search for circles that are tangent to the contours in two points; and estimate a line that joins respective centers of the circles, wherein the estimated line provides information related to an axial direction.

Clause 18. The non-transitory computer-readable storage medium of any of clauses 13-17, wherein the instructions further cause the one or more devices to: analyze, based on the sagittal direction, the femur, and determine a sagittal view of the femur; determine, based on the sagittal view, an axial direction; determine a coronal direction based on a cross-product of the sagittal and axial directions; and determine an anatomical reference frame (ARF) of the femur based on the sagittal, axial and coronal directions.

Clause 19. A device comprising: one or more processors configured to implement the method of clauses 1-12 and/or to implement the instructions of clauses 13-18. Clause 20 intentionally skipped.

Clause 21. A computer-implemented method comprising: receiving, by a device, a three-dimensional model (3D model) of a proximal tibia; identifying, by a device, a first approximate tibial axis; segmenting, by a device, the 3D model using the first approximate tibial axis to create segmented data; delineating, by a device, an exterior perimeter of the tibial plateau from the segmented data; fitting, by a device, a tibial plane based on the exterior perimeter and at least a portion of the segmented data, a normal to the tibial plane defines a final tibial axis; finding, by a device, a bi-tangent line on a posterior based on the exterior perimeter and a portion of the segmented data; forming, by a device, a tibial grid comprising a rectangle having a first long edge coaxial with the bi-tangent line, a second long edge parallel to the first long edge and identifying an outermost edge of an anterior portion of the exterior perimeter, a first short edge perpendicular to the first long edge and identifying a medial-most portion of the exterior perimeter, and a second short edge perpendicular to the first long edge and identifying a lateral-most portion of the exterior perimeter; and overlaying and displaying, by a device, the tibial grid relative to the 3D model.

Clause 22. The computer-implemented method of clause 21 wherein identifying the first approximate tibial axis further comprises morphing a statistical shape model (SSM) to correspond to the 3D model to create a morphed SSM, and identifying the first approximate tibial axis from the morphed SSM.

Clause 23. The computer-implemented method of any of clauses 21-22, further comprising: identifying a nadir of the tibial plateau from the SSM; wherein segmenting further comprises segmenting the 3D model using the first approximate tibial axis and the nadir to create segmented data.

Clause 24. The computer-implemented method of clause 23 wherein segmenting the 3D model further comprises selecting data points from the 3D model that reside in and above a segmentation plane, the segmentation plane perpendicular to the first approximate tibial axis, and the segmentation plane a predetermined distance distal of nadir of the tibial plateau.

Clause 25. The computer-implemented method of clause 24 wherein the nadir of the tibial plateau is a distal-most point of a medial plateau.

Clause 26. The computer-implemented method of any of clauses 21-25, further comprising: estimating a sagittal direction of the 3D model; projecting the 3D model in the sagittal direction, resulting in a sagittal projection; finding a posterior-most point of the tibial plateau from the sagittal projection; and wherein segmenting further comprises segmenting the 3D model using the posterior-most point and the first approximate tibial axis.

Clause 27. The computer-implemented method of clause 26 wherein segmenting the 3D model further comprises selecting data points from the 3D model that reside in and above a segmentation plane, the segmentation plane perpendicular to the first approximate tibial axis, and the segmentation plane a predetermined distance distal of the posterior-most point of the tibial plateau.

Clause 28. The computer-implemented method of any of clauses 21-27, wherein delineating the exterior perimeter of the tibial plateau further comprises identifying contour regions within the segmented data, and assigning the exterior perimeter based on the contour regions.

Clause 29. The computer-implemented method of any of clauses 21-28, wherein finding the bi-tangent line further comprises: projecting the exterior perimeter and data of the segmented data within the exterior perimeter onto the tibial plane to create projected data; and finding the bi-tangent line on the posterior of the projected data.

Clause 30. The computer-implemented method of any of clauses 21-29 further comprising identifying, by a device, a tibial tuberosity within the 3D model and displaying an indication of the location of the tibial tuberosity within the 3D model.

Clause 31. The computer-implemented method of clause 30 wherein identifying the tibial tuberosity further comprises: projecting the 3D model onto a sagittal plane; segmenting the 3D model along a line perpendicular to the second long edge resulting in a tuberosity segmentation; and identifying an anterior-most portion of the tuberosity segmentation as the tibial tuberosity.

Clause 32. The computer-implemented method of any of clauses 21-31, wherein segmenting to create the segmented data further comprises selecting data proximal of a predetermined point distal of the nadir.

Clause 33. The computer-implemented method of any of clauses 21-32, wherein fitting the tibial plane further comprises fitting based on the exterior perimeter and segmented data that resides within the exterior perimeter.

Clause 34. A non-transitory computer-readable storage medium tangibly encoded with computer-executable instructions, that when executed by one or more devices, cause the one or more devices to: receive a three-dimensional model (3D model) of a proximal tibia; identify a first approximate tibial axis; segment the 3D model using the first approximate tibial axis to create segmented data; delineate an exterior perimeter of the tibial plateau from the segmented data; fit a tibial plane based on the exterior perimeter and at least a portion of the segmented data, a normal to the tibial plane defines a final tibial axis; find a bi-tangent line on a posterior based on the exterior perimeter and portion of the segmented data; form a tibial grid comprising a rectangle having a first long edge coaxial with the bi-tangent line, a second long edge parallel to the first long edge and identifying an outermost edge of an anterior portion of the exterior perimeter, a first short edge perpendicular to the first long edge and identifying a medial-most portion of the exterior perimeter, and a second short edge perpendicular to the first long edge and identifying a lateral-most portion of the exterior perimeter; and overlay and display the tibial grid relative to the 3D model.

Clause 35. The non-transitory computer-readable storage medium of clause 34, wherein when the one or more devices identify the first approximate tibial axis and the nadir of the tibial plateau, the instructions further cause the one or more devices to morph a statistical shape model (SSM) to correspond to the 3D model to create a morphed SSM, and identify the first approximate tibial axis from the morphed SSM.

Clause 36. The non-transitory computer-readable storage medium of any of clauses 34-35, wherein the instructions further cause the one or more device to identify a nadir of the tibial plateau from the SSM, and wherein when the one or more devices segment the 3D model, the instructions further cause the one or more device to segment the 3D model using the first approximate tibial axis and the nadir of the tibial plateau.

Clause 37. The non-transitory computer-readable storage medium of clause 36, wherein when the one or more devices segment the 3D model, the instructions cause the one or more devices to select data points from the 3D model that reside in and above a segmentation plane, the segmentation plane perpendicular to the first approximate tibial axis, and the segmentation plane a predetermined distance distal of nadir of the tibial plateau.

Clause 38. The non-transitory computer-readable storage medium of any of clauses 34-37, wherein the instructions further cause the one or more devices to: estimate a sagittal direction of the 3D model; project the 3D model in the sagittal direction, resulting in a sagittal projection; and find a posterior-most point of the tibial plateau from the sagittal projection; when the one or more devices segment the 3D model, the instructions cause the one or more device to segment the 3D model using the posterior-most point and the first approximate tibial axis.

Clause 39. The computer-implemented method of any of clauses 34-38, wherein when the one or more device segment the 3D model, the instructions further cause the one or more device to select data points from the 3D model that reside in and above a segmentation plane, the segmentation plane perpendicular to the first approximate tibial axis, and the segmentation plane a predetermined distance distal of the posterior-most point of the tibial plateau.

Clause 40. The non-transitory computer-readable storage medium of any of clauses 34-39, wherein when the one or more devices delineate the exterior perimeter of the tibial plateau, the instructions further cause the one or more devices to identify contour regions within the segmented data, and assign the exterior perimeter based on the contour regions.

Clause 41. The non-transitory computer-readable storage medium of any of clauses 34-40, wherein when the one or more devices find the bi-tangent line, the instructions further cause the one or more devices to: project the exterior perimeter and the data points of the segmented data within the exterior perimeter onto the tibial plane to create projected data; and find the bi-tangent line on the posterior of the projected data.

Clause 42. The non-transitory computer-readable storage medium of any of clauses 34-41, wherein the instructions further cause the one or more devices to identify a tibial tuberosity within the 3D model and display an indication of the location of the tibial tuberosity grid within the 3D model.

Clause 43. The non-transitory computer-readable storage medium of clause 42, wherein when the one or more devices identify the tibial tuberosity, the instructions cause the one or more devices to: project the 3D model onto a sagittal plane; segment the 3D model along a line perpendicular to the second long edge resulting in a tuberosity segmentation; and identify an anterior-most portion of the tuberosity segmentation as the tibial tuberosity.

Clause 44. The non-transitory computer-readable storage medium of any of clauses 34-43, wherein when the one or more devices segment to create the segmented data, the instructions further cause the one or more devices to select data proximal of a predetermined point distal of the nadir.

Clause 45. The non-transitory computer-readable storage medium of any of clauses 34-44, wherein when the one or more devices fit the tibial plane, the instructions cause the one or more devices to fit based on the exterior perimeter and segmented data that resides within the exterior perimeter.

Clause 46. A device comprising: one or more processors configured to implement the method of clauses 21-33 and/or to implement the instructions of clauses 34-45.

What is claimed is:

1. A computer-implemented method, comprising:
using one or more computing devices:
receiving a three-dimensional (3D) model of a proximal tibia;
identifying a first approximate tibial axis;
segmenting the 3D model using the first approximate tibial axis to create segmented data;
delineating an exterior perimeter of a tibial plateau from the segmented data;
fitting a tibial plane based on the exterior perimeter of the tibial plateau and at least a portion of the segmented data, wherein a normal to the tibial plane defines a final tibial axis;
finding a bi-tangent line on a posterior based on the exterior perimeter of the tibial plateau and a portion of the segmented data;
forming a tibial grid comprising a rectangle having a first long edge coaxial with the bi-tangent line, a second long edge parallel to the first long edge and identifying an outermost edge of an anterior portion of the exterior perimeter of the tibial plateau, a first short edge perpendicular to the first long edge and identifying a medial-most portion of the exterior perimeter of the tibial plateau, and a second short edge perpendicular to the first long edge and identifying a lateral-most portion of the exterior perimeter of the tibial plateau; and
overlaying and displaying the tibial grid relative to the 3D model.

2. The computer-implemented method of claim 1, wherein identifying the first approximate tibial axis further comprises morphing a statistical shape model (SSM) to correspond to the 3D model to create a morphed SSM, and identifying the first approximate tibial axis from the morphed SSM.

3. The computer-implemented method of claim 2, further comprising:
identifying a nadir of the tibial plateau from the SSM;
wherein segmenting the 3D model further comprises segmenting the 3D model using the first approximate tibial axis and the nadir to create the segmented data.

4. The computer-implemented method of claim 3, wherein segmenting the 3D model further comprises selecting data points from the 3D model that reside in and above a segmentation plane, the segmentation plane perpendicular to the first approximate tibial axis, and the segmentation plane a predetermined distance distal of the nadir of the tibial plateau.

5. The computer-implemented method of claim 4, wherein the nadir of the tibial plateau is a distal-most point of a medial plateau.

6. The computer-implemented method of claim 1, further comprising:
estimating a sagittal direction of the 3D model;
projecting the 3D model in the sagittal direction, resulting in a sagittal projection; and
finding a posterior-most point of the tibial plateau from the sagittal projection,
wherein segmenting further comprises segmenting the 3D model using the posterior-most point and the first approximate tibial axis.

7. The computer-implemented method of claim 6, wherein segmenting the 3D model further comprises selecting data points from the 3D model that reside in and above a segmentation plane, the segmentation plane perpendicular to the first approximate tibial axis, and the segmentation plane a predetermined distance distal of the posterior-most point of the tibial plateau.

8. The computer-implemented method of claim 1, wherein delineating the exterior perimeter of the tibial plateau further comprises identifying contour regions within the segmented data, and assigning the exterior perimeter of the tibial plateau based on the contour regions.

9. The computer-implemented method of claim 1, wherein finding the bi-tangent line further comprises:
projecting the exterior perimeter of the tibial plateau and data of the segmented data within the exterior perimeter of the tibial plateau onto the tibial plane to create projected data; and
finding the bi-tangent line on the posterior of the projected data.

10. The computer-implemented method of claim 1, further comprising identifying a tibial tuberosity within the 3D model and displaying an indication of a location of the tibial tuberosity within the 3D model.

11. The computer-implemented method of claim 10, wherein identifying the tibial tuberosity further comprises:
projecting the 3D model onto a sagittal plane;
segmenting the 3D model along a line perpendicular to the second long edge resulting in a tuberosity segmentation; and
identifying an anterior-most portion of the tuberosity segmentation as the tibial tuberosity.

12. The computer-implemented method of claim 11, wherein segmenting to create the segmented data further comprises selecting data proximal of a predetermined point distal of a nadir of the tibial plateau.

13. The computer-implemented method of claim 11, wherein fitting the tibial plane further comprises fitting based on the exterior perimeter of the tibial plateau and the segmented data that resides within the exterior perimeter of the tibial plateau.

14. A device, comprising:
one or more processors configured to:
receive a three-dimensional model (3D model) of a proximal tibia;
identify a first approximate tibial axis;
segment the 3D model using the first approximate tibial axis to create segmented data;
delineate an exterior perimeter of a tibial plateau from the segmented data;
fit a tibial plane based on the exterior perimeter of the tibial plateau and at least a portion of the segmented data, a normal to the tibial plane defines a final tibial axis;

find a bi-tangent line on a posterior based on the exterior perimeter of the tibial plateau and portion of the segmented data;

form a tibial grid comprising a rectangle having a first long edge coaxial with the bi-tangent line, a second long edge parallel to the first long edge and identifying an outermost edge of an anterior portion of the exterior perimeter of the tibial plateau, a first short edge perpendicular to the first long edge and identifying a medial-most portion of the exterior perimeter of the tibial plateau, and a second short edge perpendicular to the first long edge and identifying a lateral-most portion of the exterior perimeter of the tibial plateau; and overlay and display the tibial grid relative to the 3D model.

15. The device of claim 14, wherein, when the one or more processors identify the first approximate tibial axis and a nadir of the tibial plateau, the one or more processors are further configured to morph a statistical shape model (SSM) to correspond to the 3D model to create a morphed SSM, and identify the first approximate tibial axis from the morphed SSM.

16. The device of claim 15, wherein the one or more processors are further configured to identify the nadir of the tibial plateau from the SSM, and wherein when the one or more processors segment the 3D model, the one or more processors are configured to segment the 3D model using the first approximate tibial axis and the nadir of the tibial plateau.

17. The device of claim 16, wherein when the one or more processors segment the 3D model, the one or more processors are further configured to select data points from the 3D model that reside in and above a segmentation plane, the segmentation plane perpendicular to the first approximate tibial axis, and the segmentation plane a predetermined distance distal of the nadir of the tibial plateau.

18. The device of claim 16, wherein the one or more processors are further configured to:

estimate a sagittal direction of the 3D model;

project the 3D model in the sagittal direction, resulting in a sagittal projection; and find a posterior-most point of the tibial plateau from the sagittal projection, wherein, when the one or more processors segment the 3D model, the one or more processors are further configured to segment the 3D model using the posterior-most point and the first approximate tibial axis.

19. The device of claim 14, wherein at least one of:

when the one or more processors segment the 3D model, the one or more processors are configured to select data points from the 3D model that reside in and above a segmentation plane, the segmentation plane perpendicular to the first approximate tibial axis, and the segmentation plane a predetermined distance distal of a posterior-most point of the tibial plateau;

when the one or more processors delineate the exterior perimeter of the tibial plateau, the one or more processors are further configured to identify contour regions within the segmented data and assign the exterior perimeter of the tibial plateau based on the contour regions;

when the one or more processors find the bi-tangent line, the one or more processors are further configured to project the exterior perimeter of the tibial plateau and the data points of the segmented data within the exterior perimeter of the tibial plateau onto the tibial plane to create projected data and find the bi-tangent line on the posterior of the projected data;

the one or more processors are further configured to identify a tibial tuberosity within the 3D model and display an indication of a location of the tibial tuberosity within the 3D model;

when the one or more processors identify the tibial tuberosity, the one or more processors are configured to project the 3D model onto a sagittal plane, segment the 3D model along a line perpendicular to the second long edge resulting in a tuberosity segmentation, and identify an anterior-most portion of the tuberosity segmentation as the tibial tuberosity;

when the one or more processors segment to create the segmented data, the one or more processors are further configured to select data proximal of a predetermined point distal of a nadir of the tibial plateau; and when the one or more processors fit the tibial plane, the one or more processors are configured to fit the tibial plane based on the exterior perimeter of the tibial plateau and the segmented data that resides within the exterior perimeter of the tibial plateau.

20. A non-transitory computer-readable storage medium tangibly encoded with computer-executable instructions, that when executed by one or more devices, cause the one or more devices to:

receive a three-dimensional (3D) model of a proximal tibia;

identify a first approximate tibial axis;

segment the 3D model using the first approximate tibial axis to create segmented data;

delineate an exterior perimeter of a tibial plateau from the segmented data;

fit a tibial plane based on the exterior perimeter of the tibial plateau and at least a portion of the segmented data, a normal to the tibial plane defines a final tibial axis;

find a bi-tangent line on a posterior based on the exterior perimeter of the tibial plateau and portion of the segmented data;

form a tibial grid comprising a rectangle having a first long edge coaxial with the bi-tangent line, a second long edge parallel to the first long edge and identifying an outermost edge of an anterior portion of the exterior perimeter of the tibial plateau, a first short edge perpendicular to the first long edge and identifying a medial-most portion of the exterior perimeter of the tibial plateau, and a second short edge perpendicular to the first long edge and identifying a lateral-most portion of the exterior perimeter of the tibial plateau; and overlay and display the tibial grid relative to the 3D model.

* * * * *